United States Patent
Suk et al.

(10) Patent No.: US 11,389,506 B2
(45) Date of Patent: Jul. 19, 2022

(54) COMPOSITION FOR TREATING NEUROINFLAMMATORY DISEASE COMPRISING COMPLEMENT COMPONENT 8 GAMMA PROTEIN OR FRAGMENT THEREOF

(71) Applicant: KYUNGPOOK NATIONAL UNIVERSITY INDUSTRY-ACADEMIC COOPERATION FOUNDATION, Daegu (KR)

(72) Inventors: Kyoung Ho Suk, Daegu (KR); Jong Heon Kim, Daegu (KR); Jin Han, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 0 days.

(21) Appl. No.: 17/258,707

(22) PCT Filed: Mar. 7, 2019

(86) PCT No.: PCT/KR2019/002632
§ 371 (c)(1),
(2) Date: Jan. 7, 2021

(87) PCT Pub. No.: WO2020/017725
PCT Pub. Date: Jan. 23, 2020

(65) Prior Publication Data
US 2021/0268064 A1    Sep. 2, 2021

(30) Foreign Application Priority Data
Jul. 20, 2018  (KR) .................. 10-2018-0084951

(51) Int. Cl.
*A61K 38/17*  (2006.01)
*A23L 29/281*  (2016.01)
*A61P 25/28*  (2006.01)

(52) U.S. Cl.
CPC ........ *A61K 38/1725* (2013.01); *A23L 29/281* (2016.08); *A61P 25/28* (2018.01)

(58) Field of Classification Search
None
See application file for complete search history.

(56) References Cited

U.S. PATENT DOCUMENTS 7,521,195 B1 *  4/2009  Joseloff ............ G01N 33/57423
                                                          435/7.1
2010/0314251 A1  12/2010  Goldknopf
2016/0184458 A1   6/2016  Heartlein

FOREIGN PATENT DOCUMENTS

KR       10-1393946 B1    5/2014
WO    WO 2017/132155 A1    8/2017

OTHER PUBLICATIONS

GenBank: AAA18482.1: complement C8 gamma submit precursor [*Homo sapiens*], 1994.

* cited by examiner

*Primary Examiner* — Fred H Reynolds
(74) *Attorney, Agent, or Firm* — James S. Keddie; Bozicevic, Field & Francis LLP

(57) ABSTRACT

The present invention relates to a composition for treating neuroinflammatory disease comprising a complement component 8 gamma protein or a fragment thereof, and more particularly, to use for treating neuroinflammatory disease of a complement component 8 gamma protein or a fragment thereof which exhibits an effect of reducing the expression of inflammatory cytokines in microglia.

The composition of the present invention has effects of reducing Alzheimer's abnormal behavior patterns and reducing the secretion of neuroinflammatory cytokines in brain microglia and thus can be very usefully used for development of an agent for preventing or treating neuroinflammatory disease.

4 Claims, 15 Drawing Sheets

Specification includes a Sequence Listing.

COMPOSITION FOR TREATING NEUROINFLAMMATORY DISEASE COMPRISING COMPLEMENT COMPONENT 8 GAMMA PROTEIN OR FRAGMENT THEREOF

CROSS-REFERENCE TO RELATED APPLICATIONS

This application is a § 371 national phase of International Application No. PCT/KR2019/002632, filed on Mar. 7, 2019, which claims the benefit of Korean Patent Application No. 10-2018-0084951, filed on Jul. 20, 2018, which applications are incorporated by reference herein.

TECHNICAL FIELD

The present invention relates to a composition for treating neuroinflammatory disease comprising a complement component 8 gamma protein or a fragment thereof, and more particularly, to use for treating neuroinflammatory disease of a complement component 8 gamma protein or a fragment thereof which exhibits an effect of reducing the expression of inflammatory cytokines in microglia.

BACKGROUND ART

Inflammatory responses are associated with various inflammatory mediators and immune cells in local blood vessels and body fluids when tissues (cells) are damaged or infected by external infectious agents (bacteria, fungi, viruses, and various types of allergens) to exhibit a series of complex physiological reactions such as enzyme activation, secretion of inflammatory mediators, infiltration of body fluids, cell migration, and tissue destruction, and external symptoms such as erythema, swelling, fever, and pain. In normal cases, the inflammatory response serves to restore functions of living organisms by removing external infectious agents and regenerating damaged tissues. However, if the inflammatory response is excessive or persistent because antigens are not removed or internal substances are the cause, the inflammatory response rather promotes mucosal damage, resulting in diseases such as cancer in some cases.

Recently, it has been found that the inflammatory response is one of the major mechanisms that cause neurodegeneration. In other words, microglia, immune cells in the central nervous system, may be activated by various exogenous and endogenous substances, and the activated microglia produce and release substances such as inflammatory cytokines TNF-α and IL-1β, nitric oxide, and prostaglandins, and superoxide. The production of these substances induces an immune response in the short term, but excessive production or continuous production induces the death of neighboring neurons, eventually resulting in neurodegeneration. In addition, since the substances released by dying neurons re-induce the microglial activation, neurodegeneration is caught in a continuous vicious cycle. Actually, it has been reported that the microglial activation is associated with various neurodegenerative diseases, such as Alzheimer's disease, Parkinson's disease, Huntington's disease, Lou Gehrig's disease, Creutzfelt-Jakob disease (CJD), and multiple sclerosis.

In fact, the activated microglia were observed in the brains of Alzheimer's or Parkinson's patients, and the same phenomenon was confirmed even in a Parkinson's disease animal model using 1-methyl-4-phenyl-1,2,3,6-tetratetrahydropyridine (MPTP). In addition, the activated microglia have been observed in many neurological diseases such as Huntington's disease, Lou Gehrig's disease, and local and ischemic strokes, and traumatic head injury.

The microglia are cells that perform a primary immune function in the central nervous system, and maintain a shape having thin and long branches and thin cell bodies and then change the shape into an activated shape having thick and short branches and thick cell bodies to protect the neurons from these toxins which are introduced from the outside or produced therein. The activated microglia, unlike normal microglia, activate phagocytosis and proliferate cells, and express genes of cytokines such as TNF-α, IL-1β and IL-6, chemokines, inducible nitric oxide synthase (iNOS), cyclooxygenase-2 (COX-2), etc. to produce inflammatory mediators. The microglial activation has one aspect of removing damaged cells and protecting neurons from bacteria or viruses intruded from the outside, but nitric oxide produced by iNOS, prostaglandin and TNF-α produced by COX-2, etc. are toxic even to neurons, and as a result, the microglial activation aggravates damage to neurons.

Meanwhile, a complement system plays an important role in connecting innate immunity and acquired immunity through interaction with immune cells, as well as playing a role of quickly recognizing and destroying the infectious agent by taking the first stage of innate immunity. The complement system is activated through three pathways called a classical pathway, an alternative pathway, and a lectin pathway, and then various types of complement proteins are activated. Complement proteins activate the secretion of inflammatory substances, regulate the inflammatory response by interacting with immune cells, and effectively remove external infectious agents by producing substances capable of attacking the infectious agents. Since the complement system inhibits the complement activity from being excessively increased by several types of complement regulatory proteins, maintains homeostasis, and plays a key role in various stages of inflammatory response and immune response, it is known to cause various diseases when the complement protein and the complement regulatory protein are not properly controlled.

Among various proteins belonging to the complement system, a complement component 8 (C8) is a complex consisting of alpha, beta, and gamma chains, and has been known to form a membrane attack complex (MAC) together with complement components 5, 6, 7 and 9 to be involved in various immune and inflammatory responses. In addition, it has been reported that the expression of the complement component C8 was increased in the brain of Alzheimer's disease patients (American Journal of Pathology, Vol. 154, No. 3, March 1999. Koji Yasojima et al), and it has been reported that the complement component C8 was involved in damaging the cerebrovascular integrity by amplifying a pro-inflammatory effect of amyloid (Microvascular Research 75 (2008) 411-419).

Specifically, it has been reported that the gamma chain of the complement component C8 was not involved even in the formation of the C8 complex without significantly affecting the formation of MAC (Mol Immunol. 39 (2002) 453-458). In addition, unlike the C8 alpha and beta chains, the gamma chain of the complement component C8 is classified into a lipocalin gene group in which a genetic locus is located in a lipocalin gene site (Ann Hum Genet. 60 (1996) 281-291). So far, there are no research results on the functions of the C8 gamma chain. In addition, there have been no reports of a clear association between the complement component 8 protein or a fragment thereof and the neuroinflammatory disease.

DISCLOSURE

Technical Problem

Accordingly, the present inventors have made many efforts to confirm an association between a complement component 8 gamma (C8G) and neuroinflammatory disease, and as a result, found that the C8G protein exhibited an effect of preventing or treating neuroinflammatory disease, and then completed the present invention.

Therefore, an object of the present invention is to provide a pharmaceutical composition for preventing or treating neuroinflammatory disease comprising a complement component 8-gamma protein or a fragment thereof as an active ingredient.

Further, the present invention is to provide a pharmaceutical composition for preventing or treating neuroinflammatory disease consisting of a complement component 8-gamma protein or a fragment thereof.

Further, the present invention is to provide a pharmaceutical composition for preventing or treating neuroinflammatory disease consisting essentially of a complement component 8-gamma protein or a fragment thereof.

Another object of the present invention is to provide a food composition for preventing or improving neuroinflammatory disease comprising a complement component 8-gamma protein or a fragment thereof as an active ingredient.

Further, the present invention is to provide a food composition for preventing or improving neuroinflammatory disease consisting of a complement component 8-gamma protein or a fragment thereof.

Further, the present invention is to provide a food composition for preventing or improving neuroinflammatory disease consisting essentially of a complement component 8-gamma protein or a fragment thereof.

Yet another object of the present invention is to provide use of a complement component 8-gamma protein or a fragment thereof for preparing an agent for preventing or treating neuroinflammatory disease.

Still another object of the present invention is to provide a method for preventing or treating neuroinflammatory disease characterized by administering an effective dose of a composition comprising a complement component 8-gamma protein or a fragment thereof as an active ingredient to a subject in need thereof.

Further, the present invention is to provide a method for preventing or treating neuroinflammatory disease characterized by administering an effective dose of a composition consisting of a complement component 8-gamma protein or a fragment thereof to a subject in need thereof.

Further, the present invention is to provide a method for preventing or treating neuroinflammatory disease characterized by administering an effective dose of a composition consisting essentially of a complement component 8-gamma protein or a fragment thereof to a subject in need thereof.

Technical Solution

In order to achieve the object, the present invention provides a pharmaceutical composition for preventing or treating neuroinflammatory disease comprising a complement component 8-gamma protein or a fragment thereof as an active ingredient.

Further, the present invention provides a pharmaceutical composition for preventing or treating neuroinflammatory disease consisting of a complement component 8-gamma protein or a fragment thereof.

Further, the present invention provides a pharmaceutical composition for preventing or treating neuroinflammatory disease consisting essentially of a complement component 8-gamma protein or a fragment thereof.

In order to achieve another object, the present invention provides a food composition for preventing or improving neuroinflammatory disease comprising a complement component 8-gamma protein or a fragment thereof as an active ingredient.

Further, the present invention provides a food composition for preventing or improving neuroinflammatory disease consisting of a complement component 8-gamma protein or a fragment thereof.

Further, the present invention provides a food composition for preventing or improving neuroinflammatory disease consisting essentially of a complement component 8-gamma protein or a fragment thereof.

Yet another object of the present invention provides use of a complement component 8-gamma protein or a fragment thereof for preparing an agent for preventing or treating neuroinflammatory disease.

Still another object of the present invention provides a method for preventing or treating neuroinflammatory disease characterized by administering an effective dose of a composition comprising a complement component 8-gamma protein or a fragment thereof as an active ingredient to a subject in need thereof.

Further, the present invention provides a method for preventing or treating neuroinflammatory disease characterized by administering an effective dose of a composition consisting of a complement component 8-gamma protein or a fragment thereof to a subject in need thereof.

Further, the present invention provides a method for preventing or treating neuroinflammatory disease characterized by administering an effective dose of a composition consisting essentially of a complement component 8-gamma protein or a fragment thereof to a subject in need thereof.

Hereinafter, the present invention will be described in more detail.

The present invention provides a pharmaceutical composition for preventing or treating neuroinflammatory disease comprising a complement component 8-gamma protein or a fragment thereof.

Further, the present invention provides a pharmaceutical composition for preventing or treating neuroinflammatory disease consisting of a complement component 8-gamma protein or a fragment thereof.

Further, the present invention provides a pharmaceutical composition for preventing or treating neuroinflammatory disease consisting essentially of a complement component 8-gamma protein or a fragment thereof.

In the present invention, an amino acid sequence of the complement component 8-gamma (hereinafter referred to as "C8G") may be confirmed in the GenBank accession No. EAW88316.1.

Preferably, in the present invention, the C8G protein may have an amino acid sequence defined by SEQ ID NO: 1.

```
                                              [SEQ ID NO: 1]
mlppgtatll tlllaagslg qkpqrprrpa spistiqpka nfdaqqfagt wllvavgsac rflqeqghra eattlhvapq gtamaystfr kldgicwqvr qlygdtgvlg rfllqargar gavhvvvaet dyqsfavlyl eragqlsvkl yarslpvsds vlsgfeqrvq eahltedqif yfpkygfcea adqfhvldev rr
```

According to conventional reports, it has been reported that the complement component 8, one of components constituting MAC, had an increased expression in the brain of Alzheimer's disease patients (American Journal of Pathology, Vol. 154, No. 3, March 1999. Koji Yasojima et al), and was involved in damaging the cerebrovascular integrity by amplifying a pro-inflammatory effect of amyloid (Microvascular Research 75 (2008) 411-419).

In general, in the case of a protein of which expression is increased in a specific disease, an increase in expression of the protein is closely associated with a pathologic mechanism, and inhibition of the increase in expression of the protein is often recognized as a treatment method for the disease. However, according to an embodiment of the present invention, it was confirmed that the degree of neuroinflammation by LPS administration was significantly increased in a mouse in which the expression of C8G was reduced using shRNA, compared to a wild-type mouse. In addition, as a result of administering a recombinant C8G protein to a mouse induced with neuroinflammation and neurological disease by injecting LPS, abnormal behavioral patterns caused by neuroinflammation were reduced, and as a result of treating the recombinant C8G protein to microglia stimulated by LPS, it was confirmed that the expression of inflammatory cytokines was reduced.

That is, among fragments constituting the C8 protein of which the expression is increased in neuroinflammatory disease, it can be seen that the expression of the C8G protein is increased as a series of compensatory actions to resolve the pathological process of the diseases. Accordingly, a composition including the C8G protein or a fragment thereof may exhibit an effect of preventing or treating neuroinflammatory disease.

In the present invention, the "fragment" refers to a part of a C8G amino acid sequence, and refers to a polypeptide having sequence homology with an amino acid sequence of the protein of 50% or more, preferably 60% or more, more preferably 70% or more, much more preferably 80%, most preferably 90% or more.

In the present invention, it should be interpreted that the C8G protein includes a variant or functional equivalent thereof. The protein variant or functional equivalent refers to a polypeptide that has sequence homology with an amino acid sequence of the C8G protein of 60%, preferably 70%, more preferably 80% or more and exhibits substantially homogeneous activity with the C8G protein of the present invention, as a result of the addition, substitution or deletion of amino acids. The functional equivalent may include, for example, an amino acid sequence variant in which some amino acids in the amino acid sequence of the C8G protein are substituted, deleted or added. The substitution of amino acids may be preferably conservative substitution, and examples of the conservative substitution of amino acids present in nature are as follows; aliphatic amino acids (Gly, Ala, Pro), hydrophobic amino acids (Ile, Leu, Val), aromatic amino acids (Phe, Tyr, Trp), acidic amino acids (Asp, Glu), basic amino acids (His, Lys, Arg, Gln, Asn) and sulfur-containing amino acids (Cys, Met). The deletion of amino acids may preferably be located at a portion which is not directly involved in the activity of the C8G protein of the present invention. In addition, the range of the functional equivalent may include polypeptide derivatives in which some chemical structures of the polypeptide are modified while maintaining a basic backbone of the C8G protein and its physiological activity. For example, the functional equivalent may include fusion proteins and the like, which are prepared by fusion with other proteins while maintaining structural changes and physiological activity to alter the stability, storage, volatility or solubility of the C8G protein of the present invention.

In addition, the C8G protein according to the present invention may be used by itself or in the form of a pharmaceutically acceptable salt. In the present invention, the 'pharmaceutically acceptable' generally means a form which is physiologically acceptable, but does not inhibit effects of active ingredients when administered to the human, and does not cause an allergic response such as gastroenteric disorder and dizziness or similar responses thereto. As the salt, an acid addition salt formed by a pharmaceutically acceptable free acid is preferable, and as the free acid, an organic acid and an inorganic acid may be used. The organic acid is not limited thereto, but includes citric acid, acetic acid, lactic acid, tartaric acid, maleic acid, fumaric acid, formic acid, propionic acid, oxalic acid, trifluoroacetic acid, benzoic acid, gluconic acid, metasulfonic acid, glycolic acid, succinic acid, 4-toluenesulfonic acid, glutamic acid, and aspartic acid. Further, the inorganic acid is not limited thereto, but includes hydrochloric acid, bromic acid, sulfuric acid, and phosphoric acid.

In the present invention, the C8G protein or a fragment thereof may be extracted or synthesized (Merrifleld, J. Amer. chem. Soc. 85:2149-2156, 1963) from the nature, or prepared by a genetic recombination method based on a DNA sequence.

Further, the present invention provides a pharmaceutical composition for preventing or treating neuroinflammatory disease comprising a vector containing a polynucleotide encoding the C8G protein defined by SEQ ID NO: 1 or a fragment thereof, or a cell containing the vector as an active ingredient.

In the present invention, the vector may be selected from the group consisting of linear DNA, plasmid DNA, and recombinant viral vectors, and the virus may be selected from the group consisting of retrovirus, adenovirus, adeno-associated virus, herpes simplex virus, and lentivirus.

The cell containing the vector is preferably selected from the group consisting of hematopoietic stem cell, dendritic cell, autologous tumor cell, and established tumor cell, but are not limited thereto.

In the present invention, the neuroinflammatory disease may be selected from the group consisting of Alzheimer's disease, Parkinson's disease, Niemann's disease, amyotrophic axonal sclerosis, multiple sclerosis, neuroblastoma, stroke, Lou Gehrig's disease, Huntington's disease, Creutzfeldt-Jakob disease, post-traumatic stress disorder, depression, schizophrenia, and spinal muscular atrophy, but is not limited thereto.

The composition of the present invention may further include suitable carriers, excipients, and diluents which are commonly used in the preparation of pharmaceutical compositions. The pharmaceutical composition according to the present invention may be formulated and used in the form of oral formulations such as powders, granules, tablets, capsules, suspensions, emulsions, syrups, aerosols, etc., external preparations, suppositories, and sterile injectable solutions according to a conventional method.

Suitable preparations known in the art may refer to those disclosed in a reference (Remington's Pharmaceutical Science, Mack Publishing Company, Easton Pa.).

The carriers, excipients and diluents that may be included in the pharmaceutical composition of the present invention may include may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil. When the composition is formulated, the formulation may be prepared by using diluents or excipients, such as a filler, an extender, a binder, a wetting agent, a disintegrating agent, and a surfactant, which are generally used. A solid formulation for oral administration includes tablets, pills, powders, granules, capsules, etc., and these solid formulations may be prepared by mixing at least one excipient, for example, starch, calcium carbonate, sucrose, lactose, gelatin, and the like with the extract. Further, lubricants such as magnesium stearate and talc are used in addition to simple excipients. A liquid formulation for oral administration may correspond to suspensions, oral liquids, emulsions, syrups, and the like, and may include various excipients, for example, a wetting agent, a sweetener, an aromatic agent, a preserving agent, and the like, in addition to water and liquid paraffin which are commonly used as simple diluents. A formulation for parenteral administration includes sterilized aqueous solutions, non-aqueous solvents, suspensions, emulsions, freeze-dried preparations, and suppositories. As the non-aqueous solution and the suspension, propylene glycol, polyethylene glycol, vegetable oil such as olive oil, injectable ester such as ethyl oleate, and the like may be used. As a base compound of the suppository, witepsol, macrogol, tween 61, cacao butter, laurinum, glycerogelatin, and the like may be used.

The term "administration" used herein means providing a predetermined composition of the present invention to a subject by any suitable method.

A preferable dose of the pharmaceutical composition of the present invention varies according to the condition and weight of a patient, the degree of a disease, a drug form, and the route and period of administration, but may be properly selected by those skilled in the art. For a preferable effect, the composition of the present invention may be administered in a dose of 0.001 to 1000 mg/kg per day. The administration may be performed once a day or several times a day. The dose does not limit the scope of the present invention in any aspect.

When the vector containing the polynucleotide encoding the C8G protein or a fragment thereof is included in the pharmaceutical composition of the present invention, the content of the vector is preferably 0.05 to 500 mg, more preferably 0.1 to 300 mg, and in the case of a recombinant virus containing the polynucleotide encoding the protein, the content thereof may be preferably $10^3$ to $10^{12}$ IU, but is not limited thereto.

In addition, when the cells containing the polynucleotide encoding the protein are included in the pharmaceutical composition of the present invention, $10^3$ to $10^8$ cells may be contained, but is not limited thereto.

The pharmaceutical composition of the present invention may be administered to a subject through various routes. All methods of administration may be expected and for example, may be performed by oral, rectal or intravenous, intramuscular, subcutaneous, intrauterine dural or cerebrovascular injection.

Further, the present invention provides a food composition for preventing or improving neuroinflammatory disease comprising a complement component 8-gamma protein or a fragment thereof as an active ingredient.

Further, the present invention provides a food composition for preventing or improving neuroinflammatory disease consisting of a complement component 8-gamma protein or a fragment thereof.

Further, the present invention provides a food composition for preventing or improving neuroinflammatory disease consisting essentially of a complement component 8-gamma protein or a fragment thereof.

The kind of food is not particularly limited. Examples of the food which may be added with the substances include drinks, meat, sausages, bread, biscuits, rice cakes, chocolate, candies, snacks, confectionery, pizza, ramen, other noodles, gums, dairy products including ice cream, various soups, beverages, alcohol beverages and vitamin complex, dairy products and processed dairy products, and the like, and include all health functional foods in an accepted meaning.

The C8G protein of the present invention may be added to the food as it is or used with other foods or food ingredients, and may be appropriately used according to a general method. A mixing amount of the active ingredients may be suitably determined according to the purpose of use thereof (for prevention or improvement). In general, the protein in the health food may be added in an amount of 0.1 to 90 parts by weight of the total food weight. However, in the case of long-term intake for the purpose of health and hygiene or for the purpose of health control, the amount may be equal to or greater than the range, and there is no problem in terms of safety, so that the active ingredient may be used even in an amount above the range.

A health functional beverage composition of the present invention is not particularly limited to other ingredients other than containing the protein as an essential ingredient in an indicated ratio, and may contain various flavoring agents or natural carbohydrates as an additional ingredient, like conventional beverages. Examples of the above-mentioned natural carbohydrates may include general sugars, such as monosaccharides, for example, glucose, fructose and the like; disaccharides, for example, maltose, sucrose and the like; and polysaccharides, for example, dextrin, cyclodextrin and the like, and sugar alcohols such as xylitol, sorbitol, erythritol, and the like. As flavoring agents other than those described above, natural flavoring agents (tauumatin, stevia extract (e.g., rebaudioside A, glycyrginine, etc.)), and synthetic flavoring agents (saccharin, aspartame, etc.) may be advantageously used. The ratio of the natural carbohydrates may be generally about 1 to 20 g, preferably about 5 to 12 g per 100 g of the composition of the present invention.

In addition to the ingredients, the food composition of the present invention may contain various nutrients, vitamins, minerals (electrolytes), flavoring agents such as synthetic and natural flavoring agents, coloring agents and enhancers (cheese, chocolate, etc.), pectic acid and salts thereof, alginic acid and salts thereof, organic acid, a protective colloidal thickener, a pH adjusting agent, a stabilizer, a preservative, glycerin, alcohol, a carbonic acid agent used in a carbonated drink, and the like. In addition, the food composition of the present invention may contain pulp for preparing natural fruit juice, fruit juice beverages, and vegetable beverages. These ingredients may be used independently or in combination. The ratio of these additives is not limited thereto, but is generally selected in a range of 0.1 to about 20 parts by weight per 100 parts by weight of the protein of the present invention.

The present invention provides use of a complement component 8-gamma protein or a fragment thereof for preparing an agent for preventing or treating neuroinflammatory disease.

The present invention provides a method for preventing or treating neuroinflammatory disease characterized by administering an effective dose of a composition comprising a complement component 8-gamma protein or a fragment thereof as an active ingredient to a subject in need thereof.

The present invention provides a method for preventing or treating neuroinflammatory disease characterized by administering an effective dose of a composition consisting of a complement component 8-gamma protein or a fragment thereof to a subject in need thereof.

The present invention provides a method for preventing or treating neuroinflammatory disease characterized by administering an effective dose of a composition essentially consisting of a complement component 8-gamma protein or a fragment thereof to a subject in need thereof.

The present invention provides use of a vector containing a polynucleotide encoding a complement component 8-gamma protein or a fragment thereof, or a cell containing the vector for preparing an agent for preventing or treating neuroinflammatory disease.

The present invention provides a method for preventing or treating neuroinflammatory disease characterized by administering an effective dose of a composition comprising a vector containing a polynucleotide encoding a complement component 8-gamma protein or a fragment thereof or cells containing the vector as an active ingredient to a subject in need thereof.

The term 'effective dose' of the present invention means an amount which exhibits effects of improving, treating, preventing, detecting, and diagnosing of neuroinflammatory disease, or inhibiting neuroinflammatory disease when administered to the subject. The 'subject' may be animals, preferably, mammals, particularly animals including humans and may also be cells, tissues, and organs derived from animals. The subject may be a patient requiring the effects.

The term 'treatment' of the present invention comprehensively refers to improving neuroinflammatory disease or symptoms of neuroinflammatory disease, and may include treating or substantially preventing these diseases, or improving the conditions thereof, and includes alleviating, treating or preventing a symptom or most of symptoms derived from neuroinflammatory disease, but is not limited thereto.

The term 'comprising' of the present invention is used in the same manner as 'containing' or 'characterizing', and does not exclude additional ingredients or steps of the method which are not mentioned in the composition or the method. The term 'consisting of' means excluding additional elements, steps or ingredients, etc., which are not separately described. The term 'consisting essentially of' means including ingredients or steps that do not substantially affect basic properties thereof in addition to the described ingredients or steps within the range of the composition or the method.

Advantageous Effects

According to the present invention, the composition comprising the complement component 8-gamma protein or the fragment thereof as the active ingredient has effects of reducing Alzheimer's abnormal behavioral patterns and reducing the secretion of neuroinflammatory cytokines in brain microglia, and thus can be very usefully used for development of agents for preventing or treating neuroinflammatory disease.

instead of the AAV-shRNA C8G virus. The mouse was sacrificed after 1 day of LPS injection.

Figure 2A:
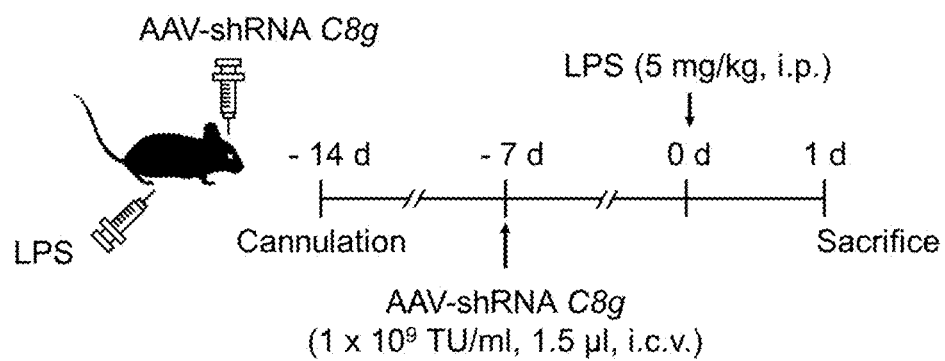
FIG. 2A illustrates an experiment for confirming an absence effect of C8G by intracerebroventricular injection of AAV-shRNA C8G virus and intraperitoneal injection of LPS in a mouse. The cannulation was performed by making a small hole in the skull at a position of 1.0 mm to the right and 0.3 mm to the rear based on Bregma and then to a depth of 1.5 mm. The AAV-shRNA C8G virus ($1 \times 10^9$ TU/ml, 1.5 μl) was injected before 7 days of LPS injection (5 mg/kg). A control was injected with AAV-shRNA Scr (Scramble)
Figure 2B:
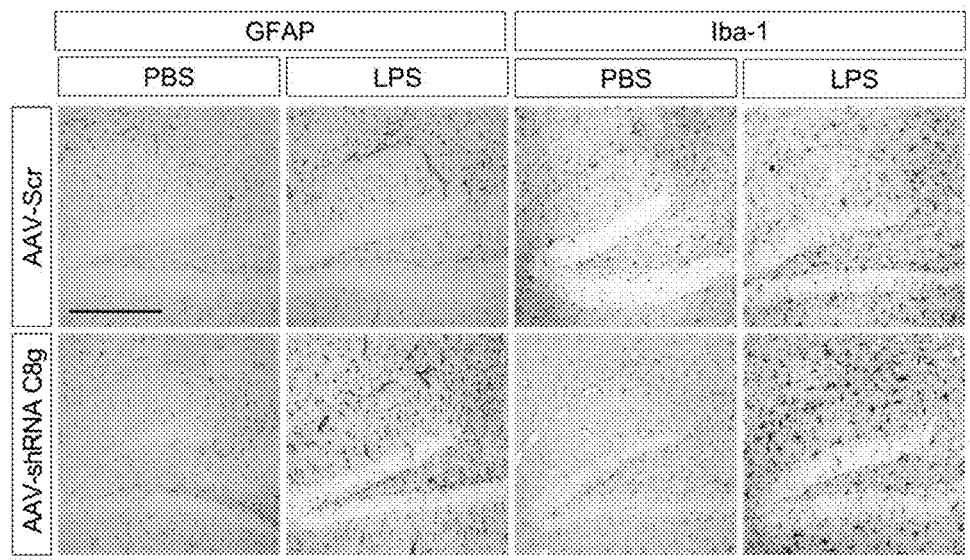

FIG. 2B illustrates a result of confirming changes in astrocytes (GFAP) and microglia (Iba-1) activated by intracerebroventricular injection of AAV-shRNA C8G virus ($1\times10^9$ TU/ml, 1.5 µl) and intraperitoneal injection of LPS (5 mg/kg) in a mouse through immunohistochemistry in the hippocampus of the mouse (Scale bar=50 µm).

Figure 2C:
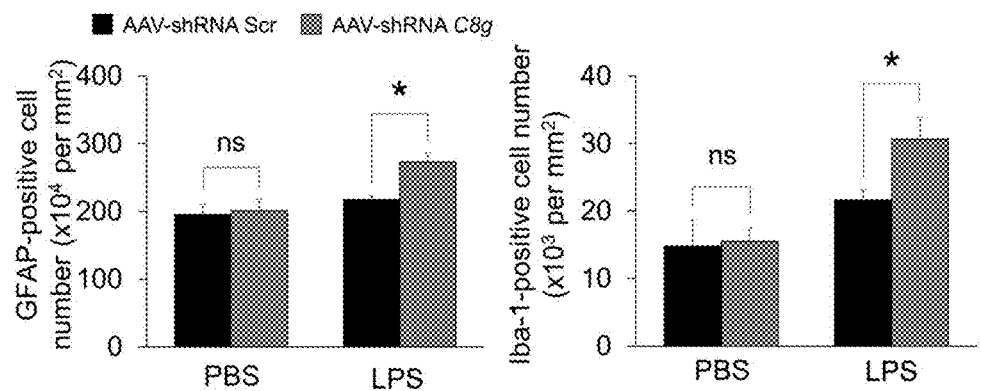

FIG. 2C is a graph showing quantification of results illustrated in FIG. 2B. The number of astrocytes (GFAP) and the number of microglia (Iba-1) activated in the hippocampus of the mouse were analyzed by an ImageJ program.

Figure 2D:
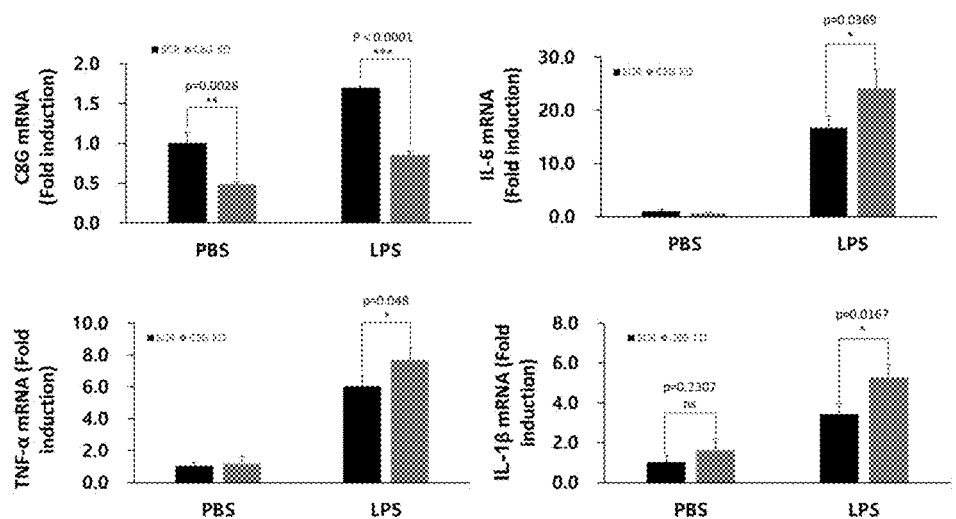

FIG. 2D illustrates a result of confirming an mRNA expression level of pro-inflammatory cytokines (IL-1β, IL-6, and TNF-α) increased by LPS by extracting the hippocampus of a C8G knockdown mouse by conventional RT-PCR.

Figure 3A:
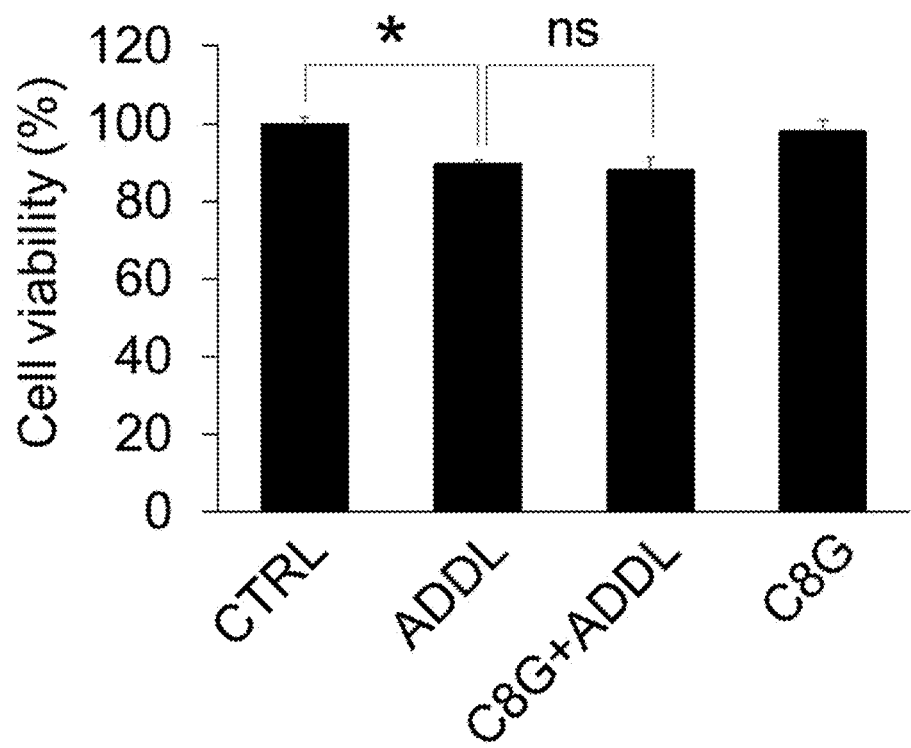

FIG. 3A is a diagram illustrating a result of measuring cytotoxicity by MTT assay after HT-22 hippocampal neurons were pre-treated with a recombinant C8G protein (1 µg/ml) for 2 hours and then treated with ADDL (2 µM) for 24 hours.

Figure 3B:
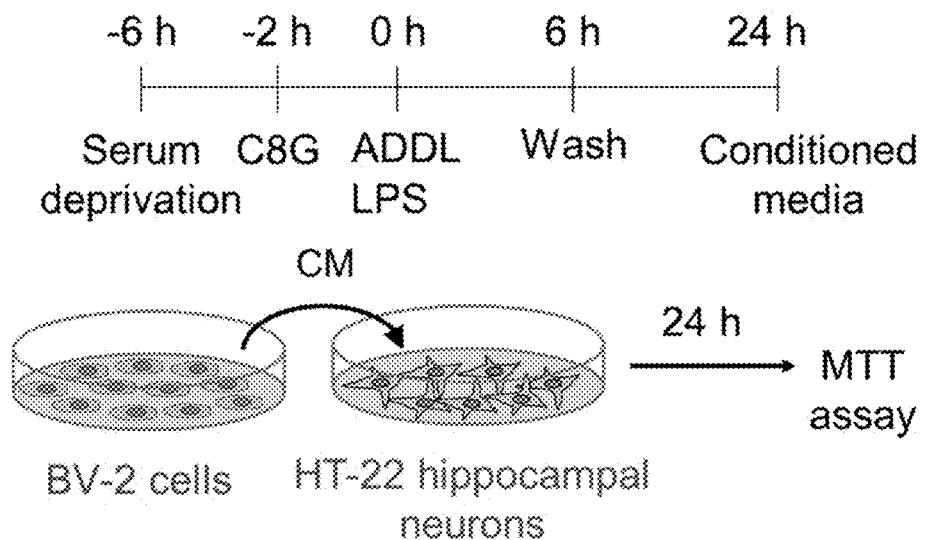

FIG. 3B illustrates an indirect toxicity experiment design. BV2 microglia were pre-treated with a recombinant C8G protein (1 µg/ml) for 2 hours, and then treated with ADDL (2 µM) and LPS (100 ng/ml) for 6 hours. Thereafter, the BV2 microglia were washed with PBS and cultured in a new serum-deprivation medium. After the treatment, conditioned media were produced for 18 hours.

Figure 3C:
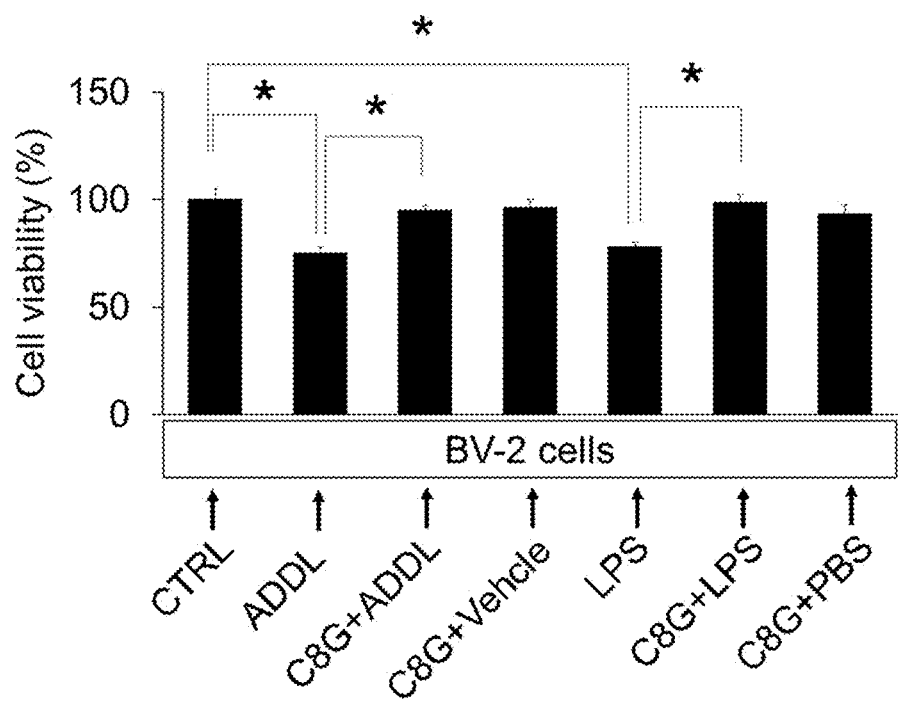

FIG. 3C is a diagram illustrating a result of measuring cytotoxicity by MTT assay by treating the conditioned media produced in FIG. 3B to HT-22 hippocampal neurons for 24 hours.

Figure 3D:
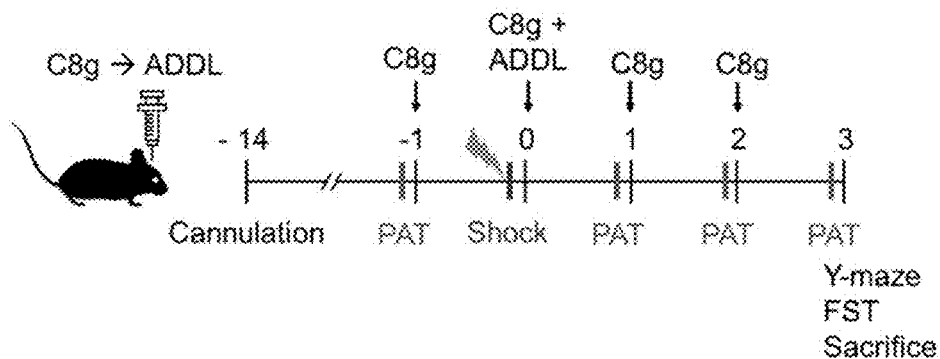

FIG. 3D illustrates an experimental design for confirming an effect of C8G using an acute Alzheimer's disease animal model in which ADDL was injected into the ventricle of a mouse. Cannulation was performed before 14 days based on the ADDL injection day. The cannulation was performed by making a small hole in the skull at a position of 1.0 mm to the right and 0.3 mm to the rear based on Bregma and then to a depth of 1.5 mm A recombinant C8G protein (1 µg/ml, 3 µl) was injected into the ventricle, and ADDL (1 µM, 7.5 µl) was injected into the ventricle after one day. At this time, a control was injected with PBS instead of ADDL. The mouse was sacrificed after a behavioral experiment at 72 hours after ADDL injection.

Figure 3E:
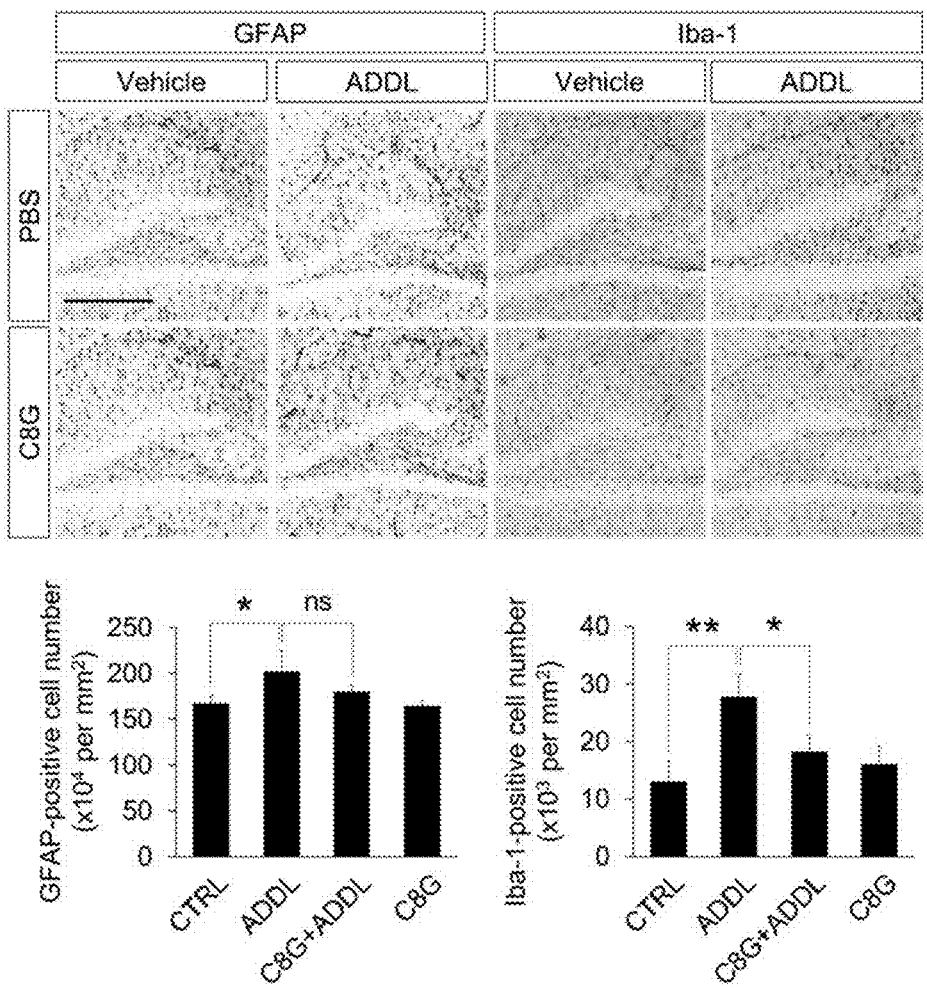

FIG. 3E is a graph showing a result of confirming changes in activated astrocytes (GFAP) and microglia (Iba-1) after 72 hours of the intracerebroventricular injection of ADDL in a mouse through immunohistochemistry in the hippocampus of the mouse and a result of quantifying the changes.

Figure 3F:
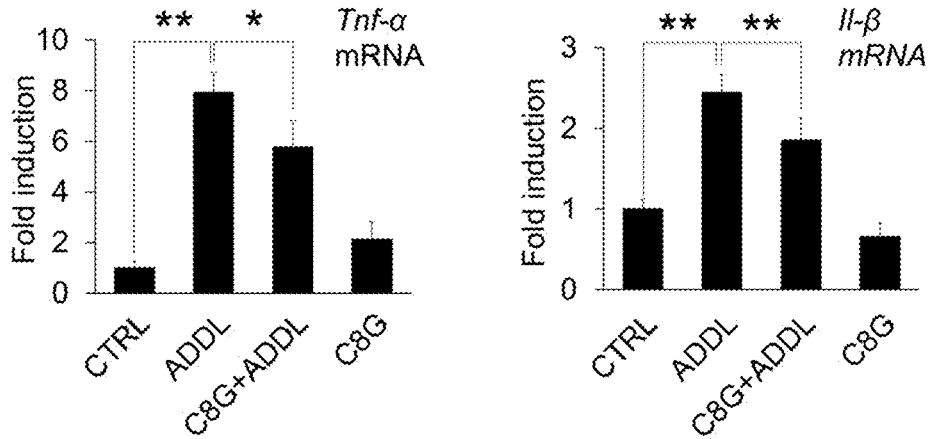

FIG. 3F illustrates a result of confirming an mRNA expression level of pro-inflammatory cytokines (TNF-α and, IL-1β) increased by ADDL by extracting the hippocampus by Conventional RT-PCR.

Figure 3G:
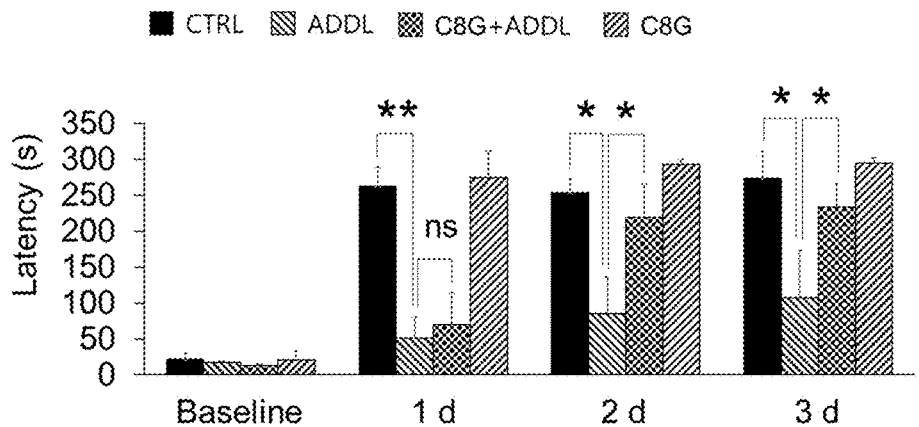

FIG. 3G illustrates a result of performing a passive avoidance test (conditioned fear test) of a mouse. After a learning session (electric shock, 0.5 mA), a movement time when the mouse entered a dark room at 24 hours (1 d), 48 hours (2 d), and 72 hours (3 d) after ADDL injection was measured.

Figure 3H:
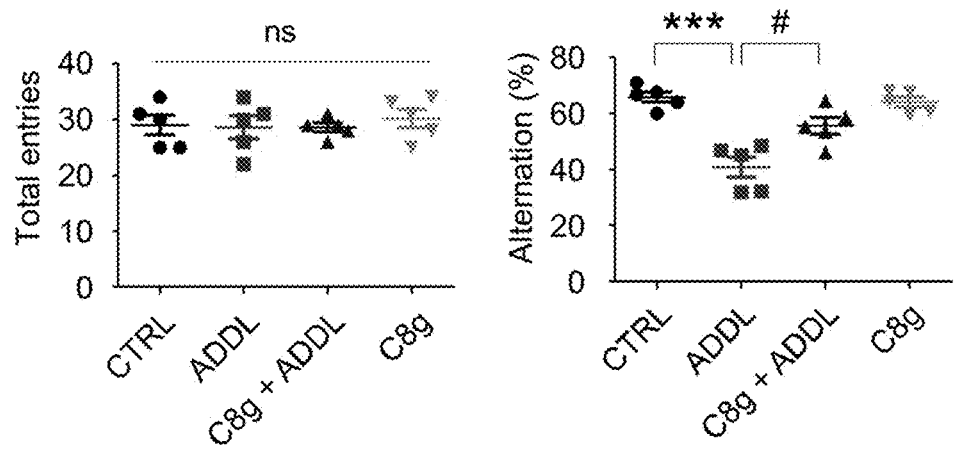

FIG. 3H illustrates a result of confirming an effect of C8G injection on a damaged spatial working memory by using an AD animal model with intracerebroventricular injection of ADDL by a Y-maze test. The spatial working memory was measured by a behavioral alternation in the Y-maze. The basic activity of the mouse was confirmed as the total number of times of passing through the Y-maze (Number of arm entries).

Figure 3I:
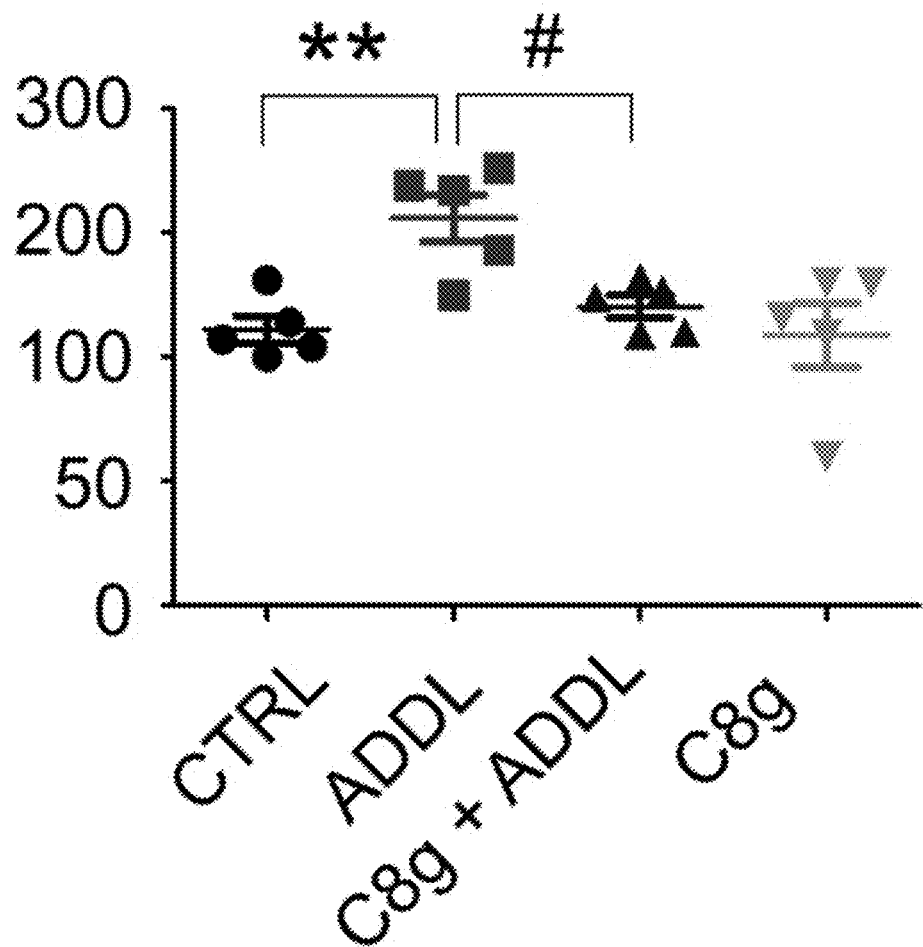

FIG. 3I illustrates a forced swim test performed to confirm an effect of C8G on depression-like symptoms shown in an AD animal model made by intracerebroventricular injection of ADDL.

Figure 4A:
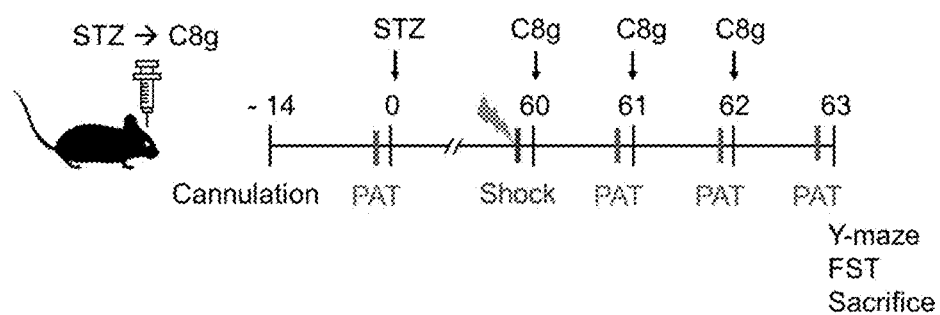

FIG. 4A illustrates an experimental design for confirming an effect of C8G using a sporadic Alzheimer's disease animal model in which STZ was injected into the ventricle in a mouse. Cannulation was performed before 14 days based on the STZ (3 mg/kg) injection day. The cannulation was performed by making a small hole in the skull at a position of 1.0 mm to the right and 0.3 mm to the rear based on Bregma and then to a depth of 1.5 mm After 60 days after the STZ injection, a recombinant C8G protein (1 µg/ml, 3 µl) was injected into the ventricle. A control was injected with saline instead of STZ. The mouse was sacrificed after a behavioral experiment at 72 hours after first C8G injection.

Figure 4B:
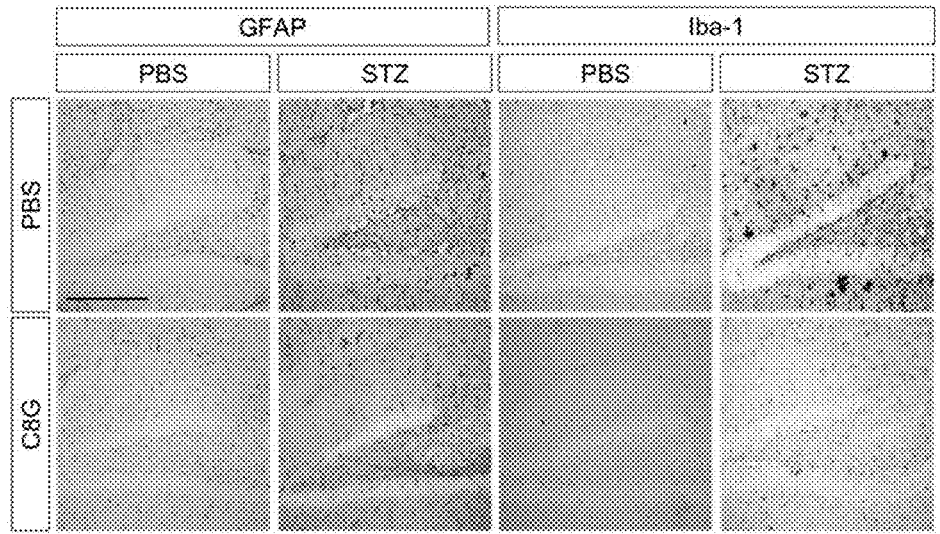

FIG. 4B illustrates a result of confirming changes in activated astrocytes (GFAP) and microglia (Iba-1) after 72 hours of the intracerebroventricular injection of C8G in a STZ-induced sporadic AD mouse through immunohistochemistry in the hippocampus of the mouse and a result of quantifying the changes.

Figure 4C:
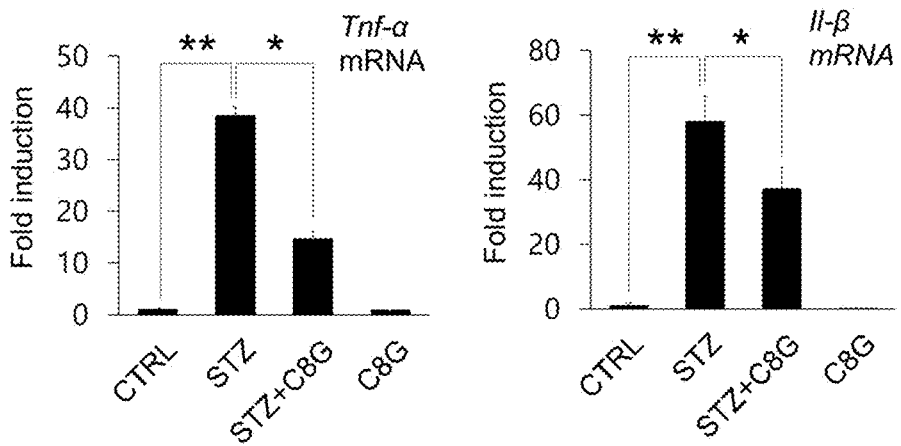

FIG. 4C illustrates results of confirming and quantifying an mRNA expression level of pro-inflammatory cytokines (TNF-α and, IL-1β) increased by STZ by extracting the hippocampus of the STZ-induced sporadic AD mouse by Conventional RT-PCR.

Figure 4D:
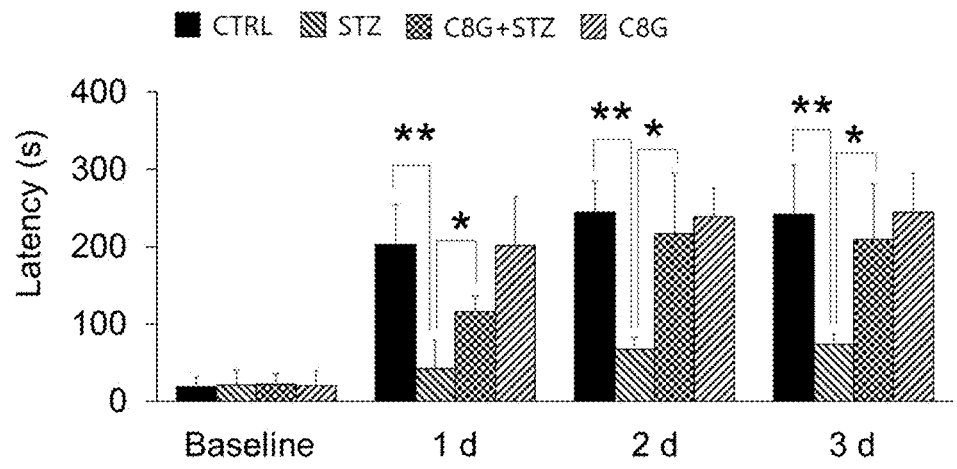

FIG. 4D illustrates a result of performing a passive avoidance test (conditioned fear test) of a mouse. After a learning session (electric shock, 0.5 mA), a movement time when the mouse entered a dark room at 24 hours (1 d), 48 hours (2 d), and 72 hours (3 d) after C8G injection was measured.

Figure 4E:
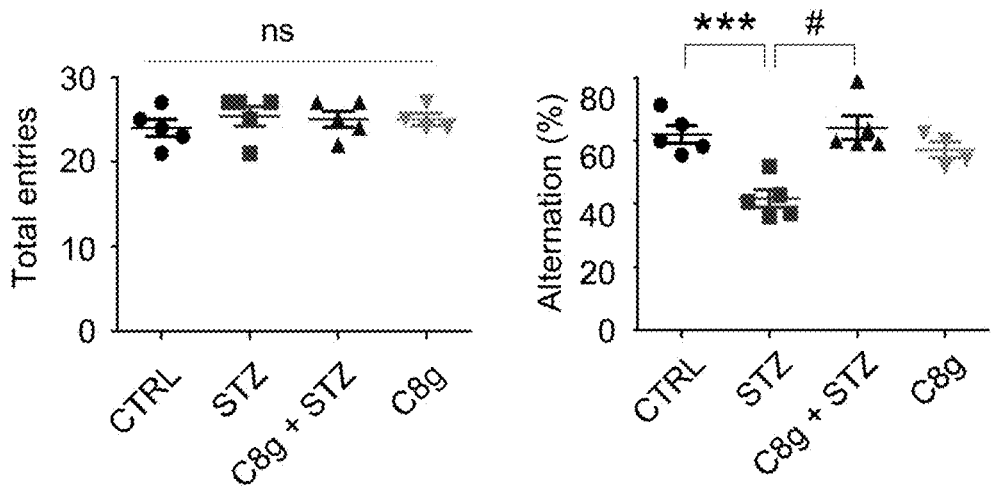

FIG. 4E illustrates a result of confirming an effect of C8G injection on a damaged spatial working memory by using a sporadic AD animal model with intracerebroventricular injection of STZ by a Y-maze test. The spatial working memory was measured by a behavioral alternation in the Y-maze.

Figure 4F:
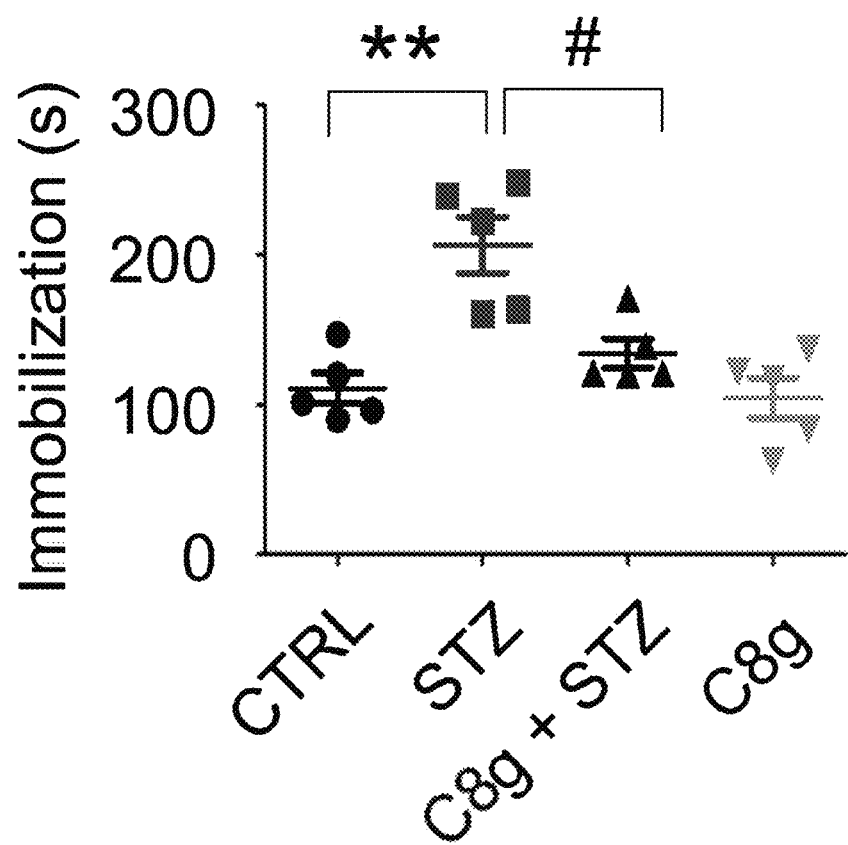

FIG. 4F illustrates a result of performing a forced swim test to confirm an effect of C8G on depression-like symptoms shown in a sporadic AD animal model made by intracerebroventricular injection of STZ.

MODE FOR CARRYING OUT INVENTION

Hereinafter, the present invention will be described in detail.

However, the following Examples are just illustrative of the present invention, and the contents of the present invention are not limited to the following Examples.

Experimental Method

1. Cell Culture

Cells used in an experiment were BV2 cells in a microglia cell line, and HT-22 cells in a hippocampal nerve cell line, and were maintained in a Dulbecco's modified Eagle medium (DMEM) supplemented with 5% bovine serum (FBS) and antibiotics. As primary cultured astrocytes, mixed neuroglia were obtained by extracting the brain from a 3-day-old mouse. After 2 weeks of culture, non-astrocytes were removed by shaking at 250 rpm.

2. Griess Assay

The level of nitric oxide, an indicator of the inflammatory response of microglia, was measured indirectly using the amount of nitrogen dioxide (NO$_2$—) due to the instability of nitric oxide. After 24 hours after inflammatory stimulation of microglia, 50 μl of a culture medium was transferred to a 96-well plate, and 50 μl of a Griess reagent (1% sulfanylamide/0.1% naphthylethylenediamine dihydrochloride/2% phosphoric acid) was mixed with the culture medium in the 96-well plate. The absorbance at 550 nm was measured using a plate reader. Using NaNO$_2$ as a standard, a NO$_2$ concentration in the culture medium was calculated.

3. MTT Assay

In order to check the viability of the cells, the cells were treated with MTT [3-(4,5-dimethylthiazol-2-yl)-2,5-diphenyltetrazolium bromide] and then cultured at 37° C. for 2 hours. An intracellular insoluble formazan crystal was completely dissolved in dimethyl sulfur monoxide (DMSO) and the absorbance was measured at 570 nm.

4. Conventional RT-PCR

RNA was isolated from cells and brain tissues according to a manufacturer's protocol using a QIAzol reagent (QIAGEN, Valencia, Calif.). PCR amplification and reverse transcription were performed using a thermal cycler (Bio-Rad, Hercules, Calif.). The primers used were as follows.

Bregma and then to a depth of 1.5 mm LPS was injected into the ventricle in a dose of 2 μg, and an oligomeric amyloid beta mixture was injected in a dose of 7.5 μl at a concentration of 1 μM. Streptozotocin (STZ) was injected in a dose of 3.0 mg/kg. The following control mouse was treated in the same manner as those described above, except for injecting PBS.

7 Immunohistochemistry

A C57BL/6 mouse was perfused with saline to remove the blood and then isolate the brain. The isolated brain was immersed in 4% paraformaldehyde (PFA) for 72 hours. To protect the frozen tissue, the brain was left for 72 hours with 30% sucrose diluted in 0.1M PBS, and then embedded in an optimal cutting temperature (OCT) compound and cut to a thickness of 20 μm. Thereafter, brain slices were left at room temperature for 1 hour with 0.1% Triton X-100, 1% BSA, and 5% normal donkey serum. The brain slices were cultured overnight at 4° C. with a primary antibody [anti-GFAP (1:200 dilution; DakoCytomation, Glostrup), anti-Iba-1 (1:200 dilution; Wako, Osaka) antibody], and cultured at room temperature for 2 hours with a secondary antibody (FITC-conjugated Donkey anti-rabbit IgG antibody; Jack-

```
IL-1β[NM_008361,Forward, 5'-GCA ACT GTT CCT GAA CTC-3' (SEQ ID

NO: 2) Reverse, 5'-CTC GGA GCC TGT AGT GCA-3' (SEQ ID NO: 3)], NO52

[NM_010927, Forward, 5'-CCC TTC CGA AGT TTC TGG CAG CAG C-3' (SEQ ID

NO: 4), Reverse, 5'-GGC TGT CAG AGC CTC GTG GCT TTG G-3' (SEQ ID NO: 5)],

TNF-cc [NM_013693, Forward, 5'-CAT CTT CTC AAA ATT CGA GTG ACA A-3'

(SEQ ID NO: 6), Reverse, 5'-ACT TGG GCA GAT TGA CCT CAG-3' (SEQ ID NO:

7)], IL-6 [NM_031168, Forward, 5'-CGG CCT TCC CTA CTT CAC AA-3' (SEQ ID

NO: 8), Reverse, 5'-TAA CGC ACT AGG TTT GCC GA-3' (SEQ ID NO: 9)], GAPDH

[NM_008084, Forward, 5'-ACC ACA GTC CAT GCC ATC AC-3' (SEQ ID NO: 10),

Reverse, 5'-TCC ACC ACC CTG TTG CTG TA-3' (SEQ ID NO: 11)]. Cxcl10

[NM_021274, Forward, 5'-GAG AGA CAT CCC GAG CCA AC-3' (SEQ ID NO: 12),

Reverse, 5'-GAG GCT CTC TGC TGT CCA TC-3' (SEQ ID NO: 13)], Cc12

[NM_011333, Forward, 5'-ATG CAG TTA ACG CCC CAC TC-3' (SEQ ID NO: 14),

Reverse, 5'-TAA GGC ATC ACA GTC CGA GTC-3' (SEQ ID NO: 15)]
```

5. Enzyme-Linked Immunosorbent Assay (ELISA)

In order to measure the concentration of TNF-α in the cultured cells, the concentration of TNF-α in the cells was measured according to a manufacturer's protocol using a sandwich ELISA Kit (R&D Systems). Specifically, each cell culture medium was placed in a 96-well plate coated with an antibody of anti-TNF-α (rat monoclonal anti-mouse TNF-a, 1:180) and left at 4° C. for 18 hours. Then, the cell culture medium reacted with a detection antibody (Goat biotinylated polyclonal antimouse TNF-a, 1:180). Color development was performed using streptavidin-horseradish peroxidase (HRP, 1:120) and 3,3',5,5'-tetramethylbenzidine (TMB). Finally, 2N H$_2$SO$_4$ was added to terminate the reaction. The absorbance at 450 nm was measured using a micro plate reader.

6. Intracerebroventricular Drug Injection Animal Model

The mouse was anesthetized with isoflurane and then fixed on a stereoscopic instrument. The drug injection was performed by making a small hole in the skull at a position of 1.0 mm to the right and 0.3 mm to the rear based on son ImmunoResearch Laboratories, West Grove, Pa.). Thereafter, counter staining was performed using gelatin containing DAPI, and images were obtained using a microscope (Leica, DM2500). Iba-1 was used as a marker for microglia, GFAP was used as a marker for astrocytes, and DAPI was used as a marker for nuclei. The images were analyzed using an Image J program.

8. Sucrose Preference Test

The sucrose intake of a C57BL/6 mouse was measured from 48 hours after intracerebral injection of LPS, and one bottle of water filled with a 1% sucrose solution and one bottle filled with water were replaced every 24 hours for 3 days. Sucrose preference was measured as follows: (A Sucrose weight)/(A Sucrose weight+A water weight)×100.

9. Knockdown of C8G Gene

In order to knock down a C8G gene, a gene of a mouse shRNA C8G sequence was inserted into a pSicoR vector using a HpaI/XhoI region. After cloning, in order to prepare AAV shRNA C8G, the gene was inserted into a pAAV-MCS vector using a MluI/BglII region.

A high-concentration recombinant AAV vector was obtained from HEK293TN cells using a helper virus-free system. An Amicon ultra-15 centrifugal filter was used to concentrate the virus.

10. Passive Avoidance Test

For a passive avoidance test, a chamber was divided into two zones (17 cm×12 cm×10 cm) of a bright chamber with an illumination and a dark chamber, and an electric grid was installed on the floor to give an electric shock. As a learning test, the mouse was adapted for 30 seconds in an illuminated chamber while the illumination was turned off, and then the illumination was turned on. When the mouse moved to the dark chamber, an electric shock was applied at 0.5 mA for 3 seconds. Thereafter, each mouse was subjected to a memory test (teat trial). The time taken to move from the illuminated chamber to the dark chamber was performed with the step-through latency limited to a maximum of 300 seconds.

11. Y Maze Test

A Y-maze test apparatus consisted of a Y-shaped maze made of an acrylic plate (40 cm width, 3 cm length, and 12 cm height), and each maze was disposed at an angle of 120° to each other. After each maze was designated as regions A, B, and C, the mouse was placed in the middle and moved freely for 7 minutes, and then the regions into which the experimental animal entered were recorded (e.g., ABC-CAB . . . ). The number and order of entering each maze were recorded to evaluate alternation behavior (%). When entering three different regions sequentially, one point (actual change, that is, in the order of ABC, BCA, CAB, etc.) was recorded. No score was not recorded if the mouse did not enter consecutively. When a next animal was tested, after removing a residual odor, the maze was thoroughly cleaned with water. The alternation behavior was calculated according to the following equation. Alternation behavior %=[(Actual alternation count)/(Total alternation count)]×100. The total alternation count was used as an indicator of exercise activity.

12. Forced Swim Test

A vertical acrylic cylinder (height: 60 cm, diameter: 20 cm) was filled with 26° C. tap water and a C57BL/6 mouse fell into the water and then the test was performed. After observing the behavior for 6 minutes, the animal was removed from the water, dried, and returned to a mouse cage. Behavioral differences were classified as follows. (1) Not moving—It was judged that the mouse did not move when passively wetted with water, and it was meant that there was only a small movement to lift its nose above the surface. (2) Climbing—it was meant that the forefoot moved upward in and out of the water along the side of a swimming chamber. (3) Swimming—Referred to necessary active movements rather than keeping its head on the water. A non-moving time was measured.

Experimental Results

1. C8G Protein Regulated the Microglial Activation

Figure 1A:
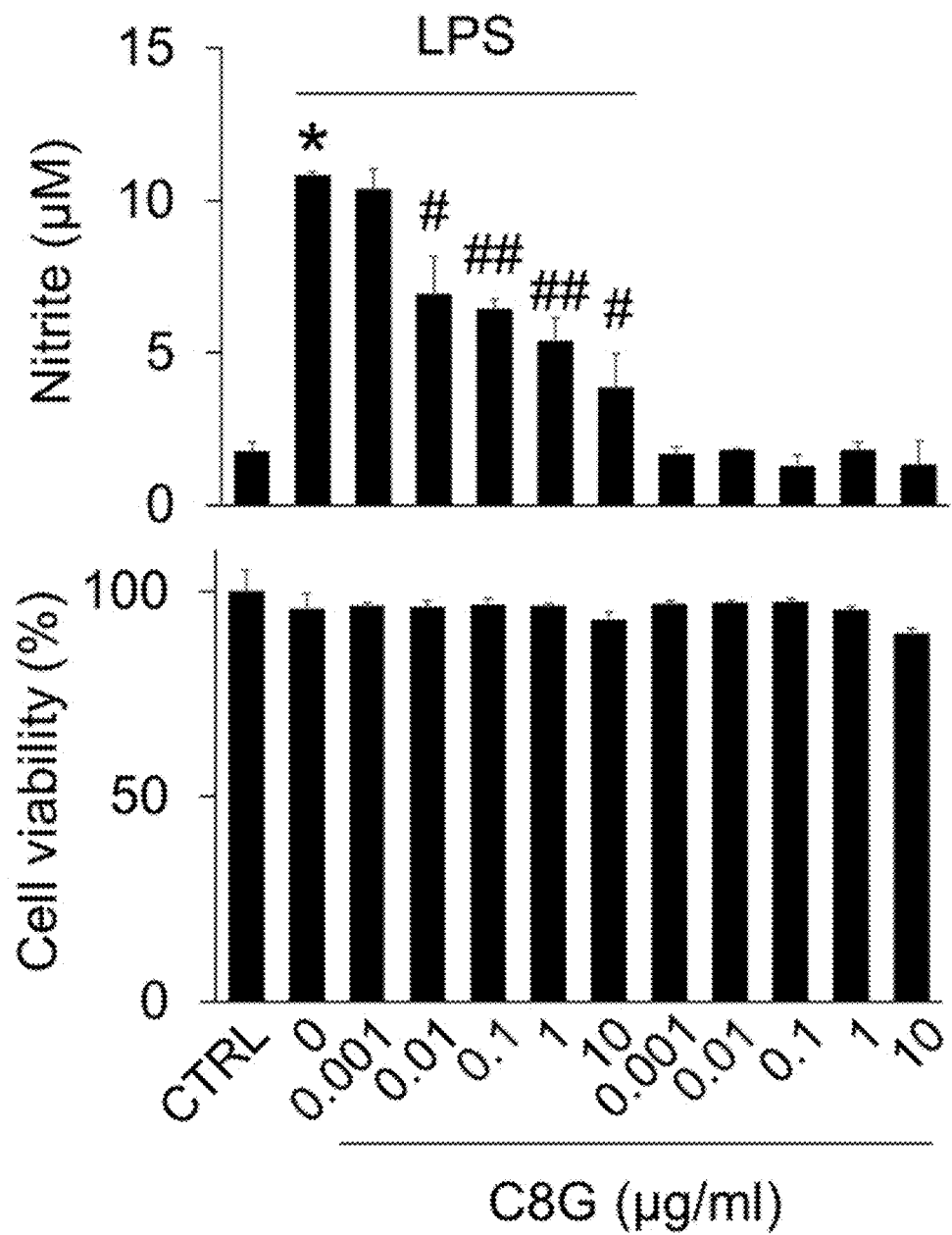
FIG. 1A illustrates a result of measuring cytotoxicity by MTT assay after BV2 microglia were pre-treated with a recombinant C8G protein for each concentration (0.001 to 10 μg/ml) and then treated with LPS (100 ng/ml) for 24 hours, and thereafter, a production level of nitrogen oxide (NO) was measured according to Griess assay (*$P<0.05$ (compared to control), #$P<0.05$, ##$P<0.01$ (compared to LPS-treated group)).

According to examination of the present inventors, there was no literature of reporting that C8G functioned as immunocalin in the brain. In order or the present inventors to confirm a potential effect of C8G on neuroinflammation, BV2 cells, microglia, were treated with a C8G recombinant protein for each dose, and then treated with LPS (100 ng/ml) after 2 hours. After 24 hours, nitric oxide (NO) and cell viability were measured using Greiss assay and MTT assay. As a result, C8G exhibited a remarkable inhibitory effect on the production of nitric oxide, which exhibited the microglial activation (inhibition concentration IC50=1 µg/ml, FIG. 1A).

Figure 1B:
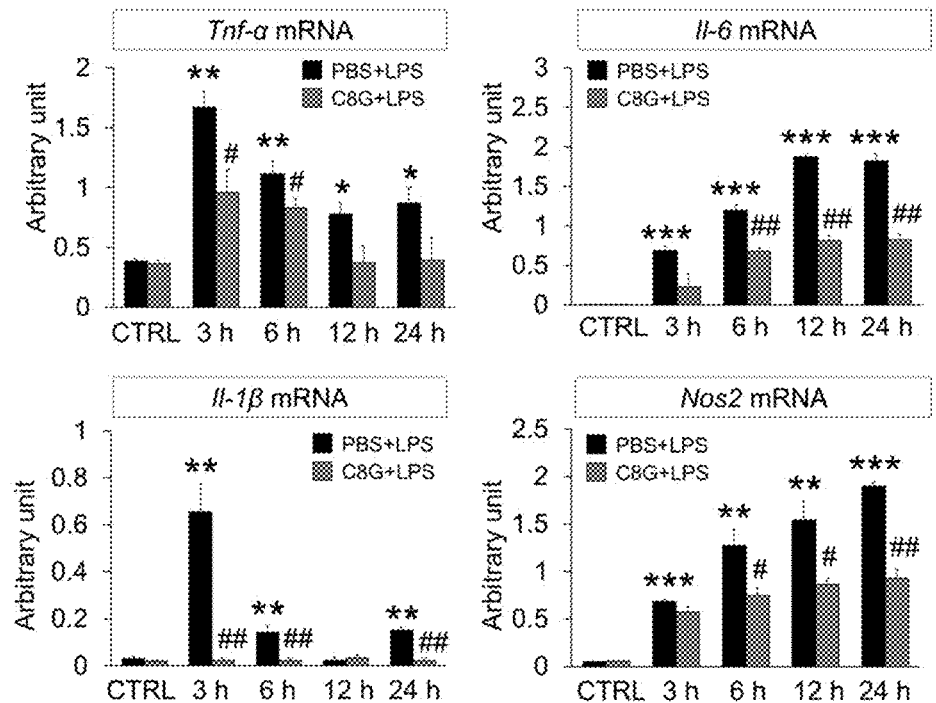
FIG. 1B is a graph showing expression levels of inflammatory cytokines and NOS2 mRNA after performing conventional RT-PCR in order to confirm whether recombinant C8G changes expression levels of proinflammatory cytokines and NOS2 mRNA increased by LPS (**$P<0.01$, *$P<0.001$ (compared to control), #$P<0.01$, ##$P<0.01$ (compared to LPS-treated group)).
Figure 1C:
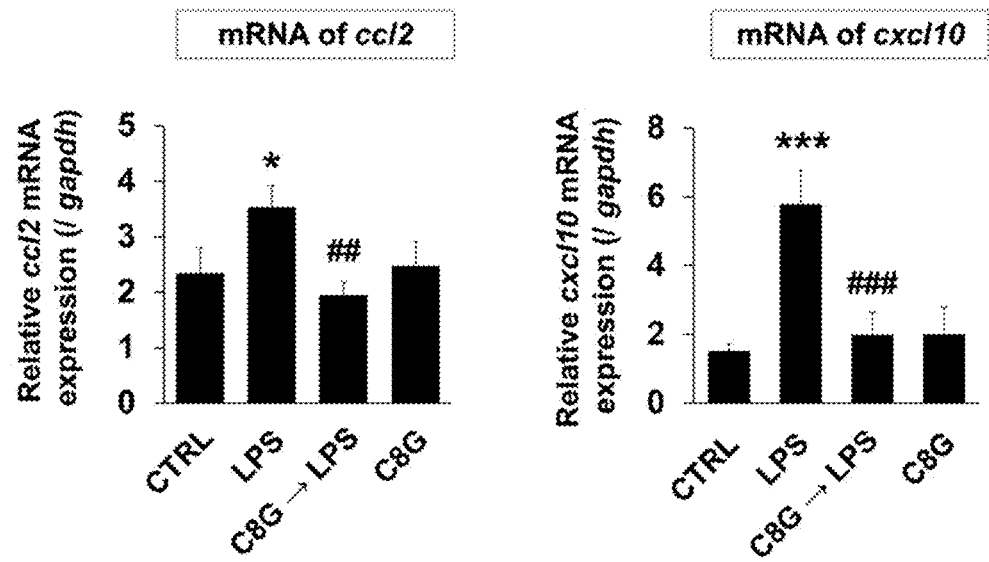
FIG. 1C illustrates a result of confirming a change in expression level of inflammation-inducing chemokine mRNA by the treatment of recombinant C8G in BV2 microglia by conventional RT-PCR (*$P<0.05$, ***$P<0.001$ (compared to control), #$P<0.01$, ##$P<0.01$ (compared to LPS-treated group).
Figure 1D:
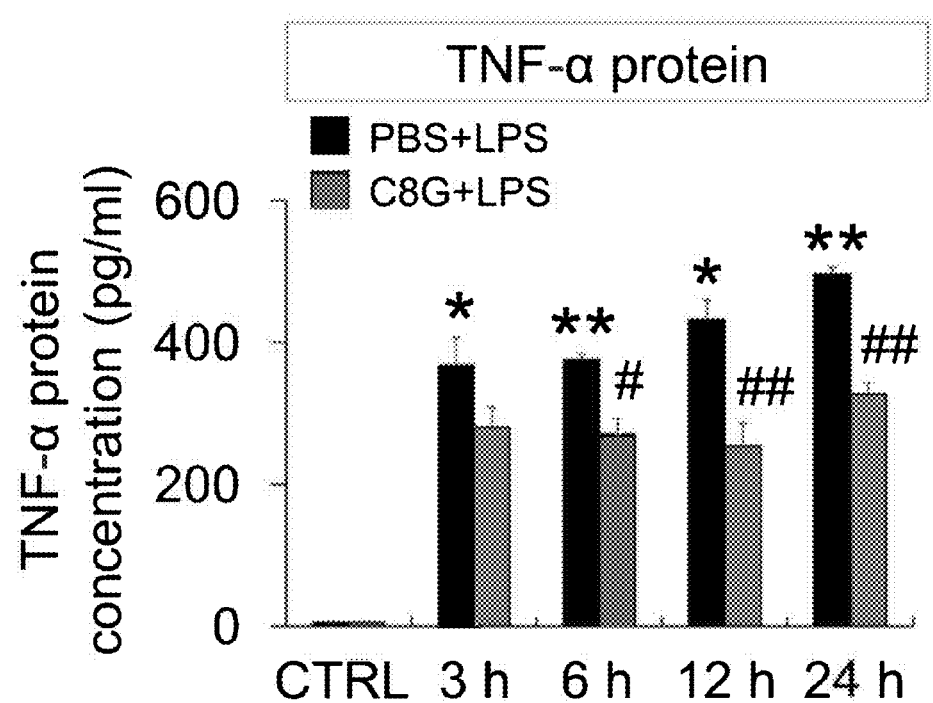
FIG. 1D illustrates a result of confirming a TNF-α protein level included in a culture medium by ELISA, by collecting a cell culture medium for each time after pre-treating a recombinant C8G protein (1 μg/ml) and then treating LPS (100 ng/ml) after 2 hours in BV2 microglia (*$P<0.05$, **$P<0.001$ (compared to control), #$P<0.05$, ##$P<0.01$ (compared to LPS-treated group).
Figure 1E:
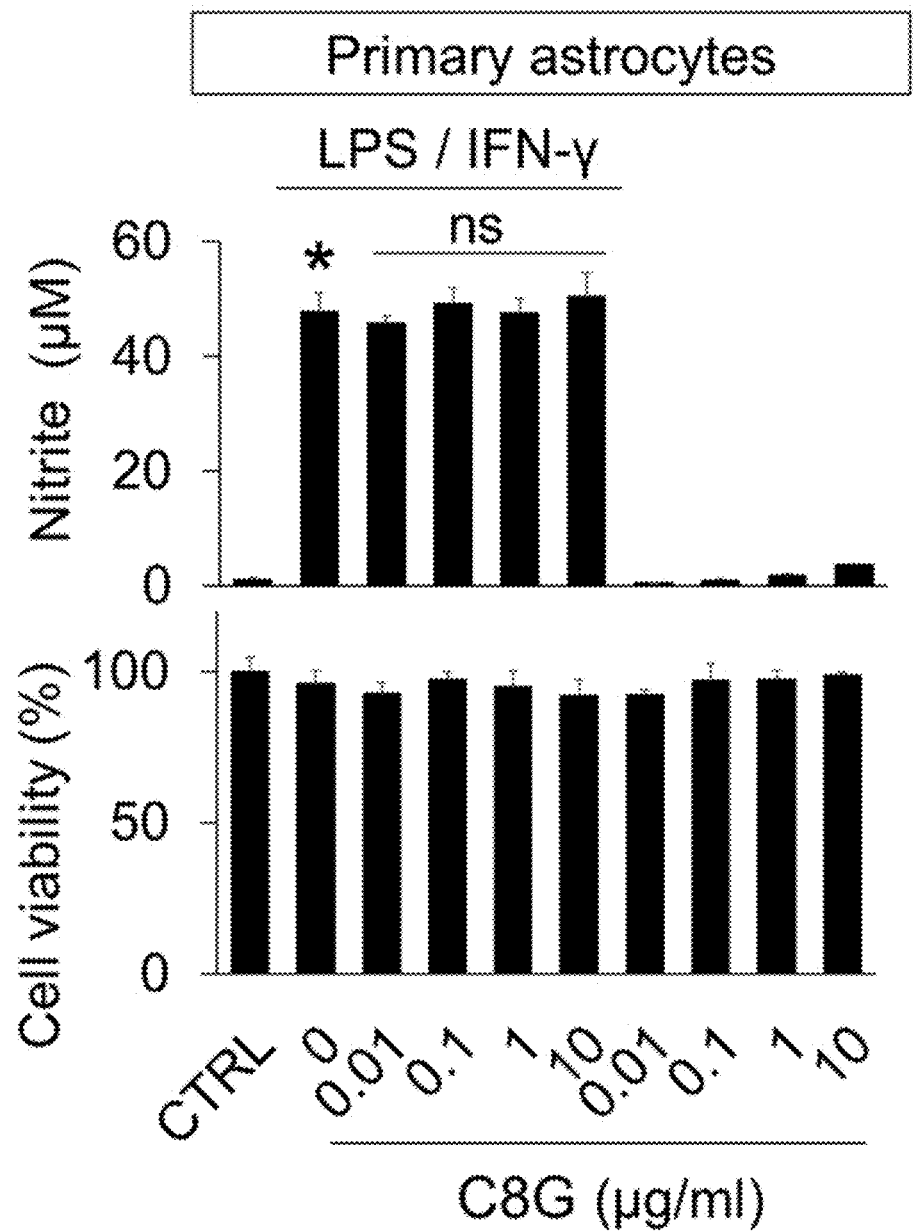
FIG. 1E illustrates a result of measuring cytotoxicity by MTT assay after astrocytes were pre-treated with a recombinant C8G protein (1 μg/ml) for 2 hours and then treated with LPS (1 μg/ml) and IFN-γ (50 units/ml) for 24 hours, and an expression level of nitrogen oxide (NO) was measured according to Griess assay.

Next, the present inventors have confirmed whether proinflammatory cytokines produced by LPS stimulation in microglia may be regulated by C8G. The BV2 cells were pre-treated with C8G (1 µg/ml) for 2 hours in the same manner as the method, and then treated with LPS (100 ng/ml). As a result of a RT-PCR test, changes in pro-inflammatory cytokines and chemokines were observed in a time-dependent manner. That is, LPS stimulation increased the production of pro-inflammatory cytokines (TNF-α, IL-1β, IL-6 and NOS2) and chemokines (CCL2 and CXCL10) (FIGS. 1B and 1C), and the production of cytokines and chemokines increased by the LPS-stimulation was inhibited by C8G treatment (FIGS. 1B to 1D). However, there was no effect on the activation of astrocytes (FIG. 1E).

Figure 1F:
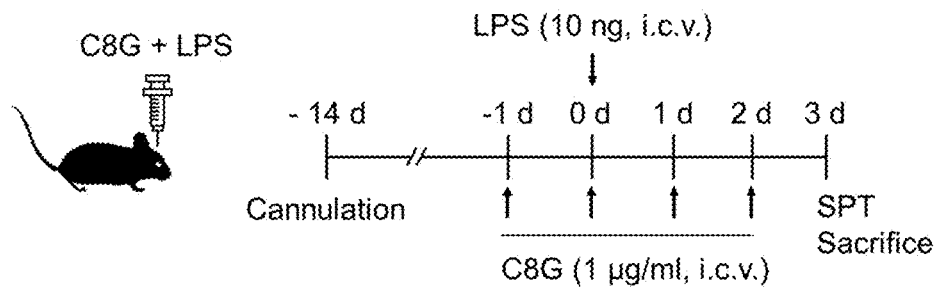
FIG. 1F illustrates an experiment for confirming an effect of the C8G recombinant protein in a neuroinflammation model induced by injecting LPS into the ventricle. Cannulation was performed before 14 days based on the LPS injection day. The cannulation was performed by making a small hole in the skull at a position of 1.0 mm to the right and 0.3 mm to the rear based on Bregma and then to a depth of 1.5 mm. The recombinant C8G protein (1 μg/ml, 3 μl) was injected into the ventricle for 4 days from a day before LPS injection (2 μg, ventricle). A control was injected with PBS instead of LPS. After 3 days of the LPS injection, a mouse was sacrificed after a depression behavioral test (sucrose preference test).
Figure 1G:
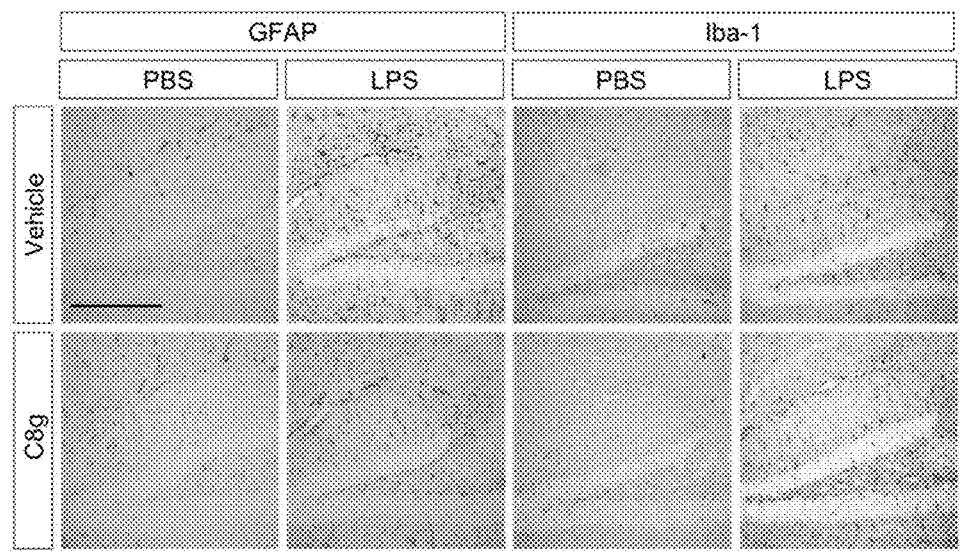
FIG. 1G illustrates a result of staining astrocytes (GFAP) and microglia (Iba-1) using immunohistochemical staining by extracting the brain of a mouse after 72 hours of intracerebroventricular injection of LPS (Scale bar=50 μm).
Figure 1H:
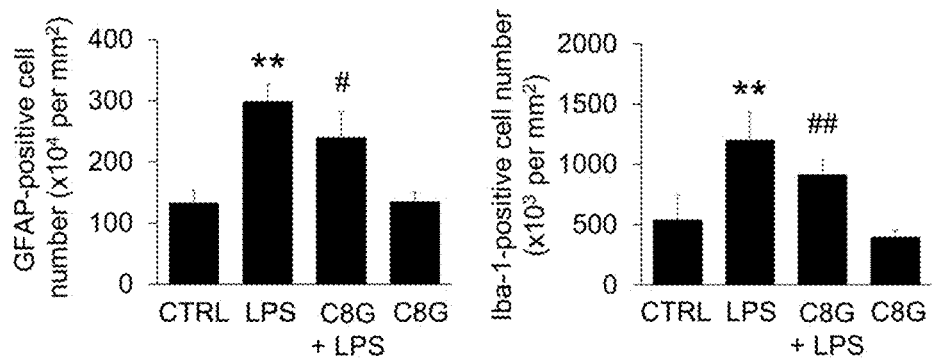
FIG. 1H illustrates a result of analyzing the number of activated astrocytes (GFAP) and the number of activated microglia (Iba-1) in the hippocampus of a mouse by an ImageJ program as illustrated in FIG. 1G.
Figure 1I:
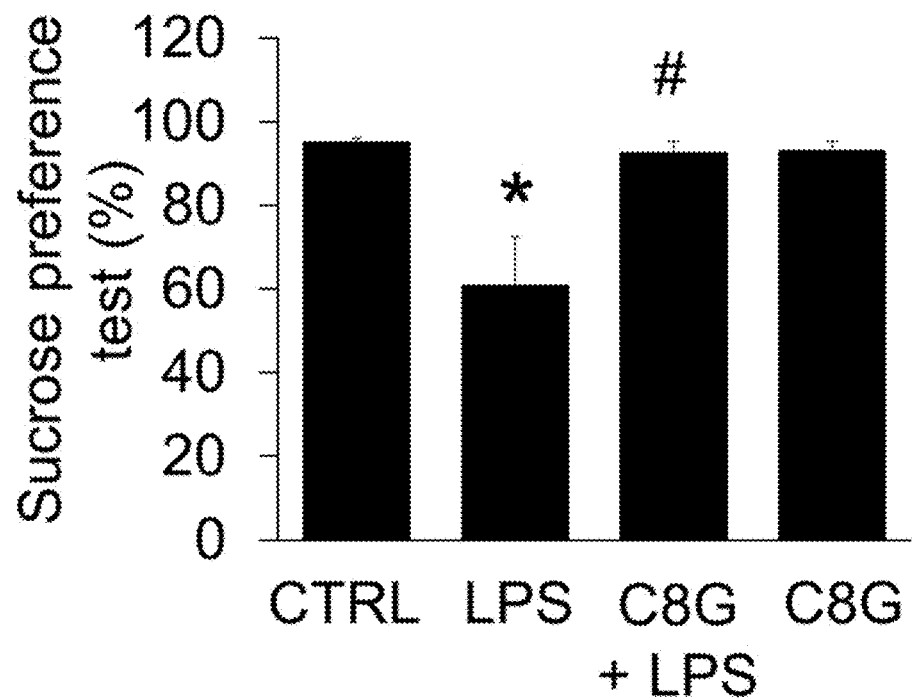
FIG. 1I is a graph showing the measurement of sucrose preference, which is a measure of a level of depression due to neuroinflammation, through a sucrose intake of a mouse after 48 hours of intracerebroventricular injection of LPS.

In order to confirm a neuroinflammation regulating effect of C8G in vivo, glial activation was measured (FIGS. 1F to 1H). The activity was measured by immunohistochemical staining. Recombinant C8G (1 µg/ml, 3 µl) was administered to a mouse injected with LPS according to a schedule shown in FIG. 1F. The morphological activation of astrocytes and microglia was remarkably increased, but the glial activation was decreased by injection of C8G (FIGS. 1G and 1H). Moreover, administration of icv-C8G alleviated behavioral patterns such as depression (sucrose preference test) (FIG. 1I).

2. In Vivo C8G Downregulation Deteriorated Systemic Neuroinflammation Induced by LPS To confirm the anti-inflammatory effect of the C8G protein confirmed in Experimental Result 1 again, the present inventors performed an experiment to confirm a change in neuroinflammation due to decreased expression of the C8G protein in the brain of a neuroinflammatory animal induced by intraperitoneal injection of LPS.

Before 7 days of LPS injection, icy AAV-shRNA C8G virus was injected ($1 \times 10^9$ TU/ml, 1.5 µl) to induce knock-down of C8G (FIG. 2A). C8G AAV-shRNA scramble ($1 \times 10^9$ TU/ml, 1.5 µl) was used as a control. As a result of the experiment, the knockdown of C8G further deteriorated microgliosis induced by LPS, but did not affect astrogliosis (FIGS. 2B and 2C), and the production of pro-inflammatory cytokines TNF-α, IL-1β, and IL-6 induced by LPS was further increased (FIG. 2D).

3. C8G Inhibited Microglial Activation Induced by Oligomeric-Amyloid Beta Mixture (ADDL) and Exhibited a Neuroprotective Effect.

The present inventors then tried to confirm whether the regulation of microglia by C8G in neuroinflammation may act as a positive effect in Alzheimer's disease (AD).

Although the AD was typically a progressive neurodegenerative disease characterized by the presence of amyloid plaques and neurofibrillary tangles, there have been many studies demonstrating that neuroinflammation was also a major cause of AD. The microglial activation played an important role in maintaining homeostasis, such as cleaning up cell debris and abnormally misfolded proteins in the early stages of AD. However, when pathological stimuli persisted chronically, the microglia converted physiological and beneficial functions. Uncontrolled microglia may directly cause synaptic loss and neurotoxicity. Thus, the regulation of microglia activation in AD could be a new treatment.

In connection with this concept, the present inventors confirmed the effect of C8G on acute neurocytotoxicity of the oligomeric-Aβ mixture (ADDL) (FIG. 3A). However, the viability of HT-22 cells as a hippocampal neuronal cell line was significantly reduced by ADDL, but C8G did not protect neurons. Accordingly, the present inventors attempted to confirm whether C8G may affect indirect toxicity to hippocampal cells. In this study, a non-contact co-culture system was used. The present inventors obtained a conditioned medium (CM) from BV2 cells cultured with ADDL or LPS for 24 hours with or without C8G pretreatment. Thereafter, the neurons were cultured with the conditioned medium for 24 hours (FIGS. 3B and 3C). As a result, when HT-22 cells were cultured in a conditioned medium without containing C8G, the cell viability significantly decreased. However, the viability of cells cultured with the conditioned medium containing C8G was similar to that of the cells of the control. The result means that C8G protects neurons from indirect toxicity induced by ADDL (FIG. 3C).

Next, the present inventors examined whether C8G may prevent hippocampal neuroinflammation and cognitive impairment in an ADDL-injected mouse. C8G was applied every 4 days from the day before icv-ADDL injection through a pre-installed icy injection cannula (FIG. 3D). In the ADDL-injected mouse, reactive astrogliosis and microgliosis of the hippocampus were clearly observed, but significantly reduced by C8G injection (FIG. 3E). In addition, the level of pro-inflammatory cytokines induced by ADDL was significantly reduced in a C8G/ADDL-injected mouse (FIG. 3F).

Next, the present inventors examined whether C8G may improve severe damage to memory caused by ADDL. In this study, the present inventors performed a passive avoidance test and a Y-maze test as a hippocampal dependent behavioral test.

In the passive avoidance test (FIG. 3G), the time taken for the mouse to move to a darker part preferred to a bright illumination of a shuttle box before exposed to an electric shock, that is, the step-through latency was not significantly different in all groups. After electric shock, the step-through latency was clearly reduced in the ADDL-injected mouse group compared to a control mouse group. This means that a response in which the electric shocked mouse remembered an unpleasant experience and avoided entering the dark room was reduced to toxicity by ADDL. In contrast, the step-through latency significantly increased from 48 hours after electric shock in a C8G/ADDL-injected mouse group compared to the ADDL-injected mouse group.

A Y-maze test of measuring a spatial working memory was performed after 1 hour of the last session of the passive avoidance test (FIG. 3H). As a result, a change in decreased impaired spatial short-term memory in the ADDL-injected mouse was significantly recovered by C8G injection.

In addition, an effect of C8G on depression-like behavior induced by ADDL injection was evaluated (FIG. 3I). Compared with the control mouse, the immobility of the ADDL-injected mouse significantly increased in a forced swim test (FST). However, the increased immobility was reduced by C8G to a level similar to that of the control.

4. C8G Alleviated Neuroinflammation and Behavioral Impairment in a Sporadic Alzheimer's Model Induced by Intracerebroventricular Injection of Streptozotocin (STZ).

In the past 20 years, transgenic mouse models produced by overexpression of genetically modified human PS1, APP and/or tau proteins have been the most used in an Alzheimer's disease study. However, these animal models have limitations without showing all the anomalies observed in human AD and showing sporadic forms of AD, which account for 99% of AD patients. Moreover, since conventional animal models exhibited acute neuropathology, there was a limitation in examining a correlation between neuroinflammation and a cause of AD.

Therefore, the present inventors used an experimental method of making a sporadic AD model by intracerebroventricular injection (icy) of streptozotocin (STZ), and tried to confirm whether injection of C8G could alleviate chronic neuroinflammation and neural death (FIG. 4A).

According to the experimental results, GFAP-positive astrocytes and Iba-1-positive microglia were significantly increased by icv-STZ and significantly decreased by C8G injection in microglia (FIG. 4B). In addition, the level of pro-inflammatory cytokines induced by STZ was significantly reduced in a STZ/C8G-injected mouse (FIG. 4C).

As a result of the passive avoidance test, the step-through latency was significantly reduced in the STZ-injected mouse group after electric shock compared to the control mouse group (FIG. 4D). However, the step-through latency increased significantly from 24 hours in the STZ+C8G-injected mouse group compared to the STZ-injected mouse group. As a result of the Y-maze test (spatial working memory), it was also confirmed that the impaired behavior shown in the STZ-injected mouse was remarkably recovered by C8G (FIG. 4E).

In addition, an effect of C8G on depression-like behavior induced by STZ injection was evaluated. Compared with the control mouse, the STZ-injected mouse significantly increased in immobility in the forced swim test (FST), while the immobility was significantly reduced by C8G (FIG. 4F).

INDUSTRIAL APPLICABILITY

According to the present invention, the composition of the present invention containing the complement component 8-gamma protein or the fragment thereof as the active ingredient has effects of reducing Alzheimer's abnormal behavior patterns and reducing the secretion of neuroinflammatory cytokines in brain microglia, and can be very usefully used for development of agents for preventing or treating neuroinflammatory disease. Therefore, the industrial applicability of the present invention is very excellent.

What is claimed is:

1. A method for reducing treating neuroinflammation, the method comprising administering an effective dose of a composition comprising a complement component 8-gamma protein having the amino acid sequence of SEQ ID NO: 1 as an active ingredient to a subject in need thereof.

2. The method of claim 1, wherein the neuroinflammation is associated with a disease selected from the group consisting of Alzheimer's disease, Parkinson's disease, Niemann's disease, amyotrophic axonal sclerosis, multiple sclerosis, neuroblastoma, stroke, Lou Gehrig's disease, Huntington's disease, Creutzfeldt-Jakob disease, post-traumatic stress disorder, depression, schizophrenia, and spinal muscular atrophy.

3. The method of claim 1, wherein the composition inhibits neuroinflammation by inhibiting the expression of inflammatory cytokines in microglia.

4. The method of claim 1, wherein the composition is a pharmaceutical composition.

* * * * *

SEQUENCE LISTING

<160> NUMBER OF SEQ ID NOS: 15

<210> SEQ ID NO 1
<211> LENGTH: 202
<212> TYPE: PRT
<213> ORGANISM: Artificial Sequence
<220> FEATURE:
<223> OTHER INFORMATION: Human complement component 8 gamma

<400> SEQUENCE: 1

Met Leu Pro Pro Gly Thr Ala Thr Leu Leu Thr Leu Leu Leu Ala Ala
1               5                   10                  15

Gly Ser Leu Gly Gln Lys Pro Gln Arg Pro Arg Arg Pro Ala Ser Pro
            20                  25                  30

```
Ile Ser Thr Ile Gln Pro Lys Ala Asn Phe Asp Ala Gln Gln Phe Ala
             35                  40                  45
Gly Thr Trp Leu Leu Val Ala Val Gly Ser Ala Cys Arg Phe Leu Gln
 50                  55                  60
Glu Gln Gly His Arg Ala Glu Ala Thr Thr Leu His Val Ala Pro Gln
65                  70                  75                  80
Gly Thr Ala Met Ala Val Ser Thr Phe Arg Lys Leu Asp Gly Ile Cys
                 85                  90                  95
Trp Gln Val Arg Gln Leu Tyr Gly Asp Thr Gly Val Leu Gly Arg Phe
                100                 105                 110
Leu Leu Gln Ala Arg Gly Ala Arg Gly Ala Val His Val Val Val Ala
            115                 120                 125
Glu Thr Asp Tyr Gln Ser Phe Ala Val Leu Tyr Leu Glu Arg Ala Gly
            130                 135                 140
Gln Leu Ser Val Lys Leu Tyr Ala Arg Ser Leu Pro Val Ser Asp Ser
145                 150                 155                 160
Val Leu Ser Gly Phe Glu Gln Arg Val Gln Glu Ala His Leu Thr Glu
                165                 170                 175
Asp Gln Ile Phe Tyr Phe Pro Lys Tyr Gly Phe Cys Glu Ala Ala Asp
            180                 185                 190
Gln Phe His Val Leu Asp Glu Val Arg Arg
            195                 200

<210> SEQ ID NO 2
<211> LENGTH: 18
<212> TYPE: DNA
<213> ORGANISM: Artificial Sequence
<220> FEATURE:
<223> OTHER INFORMATION: Synthetic oligonucleotide: IL-1 beta Forward

<400> SEQUENCE: 2
gcaactgttc ctgaactc                                                  18

<210> SEQ ID NO 3
<211> LENGTH: 18
<212> TYPE: DNA
<213> ORGANISM: Artificial Sequence
<220> FEATURE:
<223> OTHER INFORMATION: Synthetic oligonucleotide: IL-1 beta Reverse

<400> SEQUENCE: 3
ctcggagcct gtagtgca                                                  18

<210> SEQ ID NO 4
<211> LENGTH: 25
<212> TYPE: DNA
<213> ORGANISM: Artificial Sequence
<220> FEATURE:
<223> OTHER INFORMATION: Synthetic oligonucleotide: NOS2 Forward

<400> SEQUENCE: 4
cccttccgaa gtttctggca gcagc                                          25

<210> SEQ ID NO 5
<211> LENGTH: 25
<212> TYPE: DNA
<213> ORGANISM: Artificial Sequence
<220> FEATURE:
<223> OTHER INFORMATION: Synthetic oligonucleotide: NOS2 Reverse
```

```
<400> SEQUENCE: 5
ggctgtcaga gcctcgtggc tttgg                                      25

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide: TNF-alpha Foward

<400> SEQUENCE: 6
catcttctca aaattcgagt gacaa                                      25

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide: TNF-alpha Reverse

<400> SEQUENCE: 7
acttgggcag attgacctca g                                          21

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide: IL-6 Forward

<400> SEQUENCE: 8
cggccttccc tacttcacaa                                            20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide: IL-6 Reverse

<400> SEQUENCE: 9
taacgcacta ggtttgccga                                            20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide: GAPDH Forward

<400> SEQUENCE: 10
accacagtcc atgccatcac                                            20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide: GAPDH Reverse

<400> SEQUENCE: 11
tccaccaccc tgttgctgta                                            20
```

```
<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide: Cxcl10 Forward

<400> SEQUENCE: 12
gagagacatc ccgagccaac                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide: Cxcl10 Reverse

<400> SEQUENCE: 13
gaggctctct gctgtccatc                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide: Ccl2 Forward

<400> SEQUENCE: 14
atgcagttaa cgccccactc                                              20

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide: Ccl2 Reverse

<400> SEQUENCE: 15
taaggcatca cagtccgagt c                                            21
```